(12) United States Patent
Brunsvold et al.

(10) Patent No.: US 11,090,066 B2
(45) Date of Patent: Aug. 17, 2021

(54) MINIMALLY INVASIVE SURGICAL DRILL GUIDE AND METHOD

(71) Applicant: Parcus Medical, LLC, Sarasota, FL (US)

(72) Inventors: Mark D. Brunsvold, Sarasota, FL (US); Barton W. Bracy, Orlando, FL (US); Jasek Mazek, Warsaw (PL); Antonio Porthos Salas, Monterrey (MX)

(73) Assignee: PARCUS MEDICAL, LLC, Sarasota, FL (US)

( * ) Notice: Subject to any disclaimer, the term of this patent is extended or adjusted under 35 U.S.C. 154(b) by 0 days.

(21) Appl. No.: 16/588,123

(22) Filed: Sep. 30, 2019

(65) Prior Publication Data

US 2020/0100801 A1 Apr. 2, 2020

Related U.S. Application Data

(60) Provisional application No. 62/739,413, filed on Oct. 1, 2018.

(51) Int. Cl.
*A61B 17/17* (2006.01)
*A61B 90/00* (2016.01)
(Continued)

(52) U.S. Cl.
CPC ...... *A61B 17/1703* (2013.01); *A61B 17/1613* (2013.01); *A61B 17/1742* (2013.01);
(Continued)

(58) Field of Classification Search
CPC ............ A61B 17/1703; A61B 17/1613; A61B 17/1746; A61B 17/1714; A61B 17/1739; A61B 17/1742; A61B 17/175; A61B 17/1615; A61B 17/1671; A61B 17/1757; A61B 17/1697; A61B 17/1796; A61B 17/3421; A61B 17/1775; A61B 17/1682; A61B 17/320016; A61B 2017/0046;
(Continued)

(56) References Cited

U.S. PATENT DOCUMENTS 5,314,429 A * 5/1994 Goble ................ A61B 17/1714
128/898
5,573,538 A * 11/1996 Laboureau ......... A61B 17/1714
606/86 R (Continued)

*Primary Examiner* — Marcela I. Shirsat
(74) *Attorney, Agent, or Firm* — Fox Rothschild LLP

(57) ABSTRACT

A minimally invasive surgical drill guide includes an elongated drill jig having at least one drill guide opening for defining a location and drill element guide axis for placement of a surgical drill element. The drill jig can have an engagement end with engagement structure. A positioning arm includes an elongated shaft with an axis and a locating end portion shaped to engage a bony part of a patient. The elongated shaft can have engagement structure for engaging to the engagement structure of the drill jig to support the drill jig crosswise relative to the position arm and to support the drill guide opening of the drill jig at a location remote from the axis of the elongated shaft of the positioning arm. The drill jig can be detachable from the positioning arm. A method for minimally invasive surgical drilling is also disclosed.

35 Claims, 29 Drawing Sheets

(51) Int. Cl.
  *A61B 17/16* (2006.01)
  *A61F 2/08* (2006.01)
(52) U.S. Cl.
  CPC .......... *A61B 90/39* (2016.02); *A61B 17/1746* (2013.01); *A61B 2090/3966* (2016.02); *A61B 2090/3983* (2016.02); *A61F 2/0805* (2013.01)
(58) Field of Classification Search
  CPC .......... A61B 2017/1778; A61B 2017/320044; A61B 2017/320052; A61B 2017/0404; A61B 90/39; A61B 90/3966; A61B 2019/304; A61B 17/74; A61F 2/0805; A61F 2/08; A61F 2002/0882
  USPC .......................................................... 606/96
  See application file for complete search history.

(56) References Cited

U.S. PATENT DOCUMENTS

| | | | |
|---|---|---|---|
| 2009/0171355 A1* | 7/2009 | Amis ................... | A61F 2/0805 606/53 |
| 2010/0191247 A1* | 7/2010 | Schneider .......... | A61B 17/1778 606/96 |
| 2010/0241106 A1* | 9/2010 | Torrie ................ | A61B 17/3403 606/1 |
| 2015/0216542 A1* | 8/2015 | Libby ................ | A61B 17/1714 606/96 |

\* cited by examiner

MINIMALLY INVASIVE SURGICAL DRILL GUIDE AND METHOD

CROSS-REFERENCE TO RELATED APPLICATIONS

This application claims priority to U.S. Provisional Patent Application No. 62/739,413 filed on Oct. 1, 2018, entitled "Ligamentum Teres Reconstruction System And Method", the entire disclosure of which incorporated herein by reference.

FIELD OF THE INVENTION

The present invention relates to equipment and methods for surgical drilling, and more particularly for surgical drill guide apparatus and methods.

BACKGROUND OF THE INVENTION

Surgical drilling requires that the drill bit be directed very accurately to insure safe and effective outcomes. Minimally invasive surgical drilling provides additional challenges as the procedure is performed out of the direct view of the surgeon. Minimally invasive surgical drill guides and techniques have been developed for various surgical procedures. There is a need to improve upon such techniques and procedures, particularly with respect to hip joint procedures such as ligamentum teres reconstruction and avascular necrosis repair.

SUMMARY OF THE INVENTION

A minimally invasive surgical drill guide includes an elongated drill jig comprising at an engagement end thereof engagement structure. The drill jig can include a drill guide opening for defining a location and drill element guide axis for placement of a surgical drill element. A positioning arm can have an elongated shaft with an axis and a locating end portion for engaging a bony part of a patient. The shaft can include engagement structure, and the engagement structure of the drill jig can engage the engagement structure of the positioning arm crosswise or endwise to support the drill guide opening of the drill jig at a location remote from the axis of the elongated shaft. The drill jig can be detachable from the positioning arm.

The surgical drill guide can further include an elongated drill guide insert having an elongated open interior drill guide passage for receiving the surgical drill element. The drill guide insert can be dimensioned for placement in the drill guide opening of the drill jig. The drill jig and the drill guide insert can have cooperating securing structure for securing the drill guide insert within the drill guide opening.

The locating end can include a radiopaque marker. The radiopaque marker can be a radiopaque protrusion for locating the positioning arm and helping to guide the surgical drill element. The radiopaque protrusion comprises at least one radiopaque ridge. The elongated drill jig can include a plurality of drill guide openings and the locating end can include a radiopaque marker associated with each drill guide opening, where the drill element guide axis of each drill guide opening intercepts the associated radiopaque marker. The locating end can be curved. The curved locating end can be configured to mate with a portion of the femoral head. The curved locating end can be configured to mate with the fovea.

The invention includes a method for minimally invasive surgical drilling. The method includes the step of providing an elongated drill jig comprising at an engagement end thereof engagement structure, the drill jig comprising a drill guide opening for defining a location and drill element guide axis for placement of a surgical drill element. A positioning arm can have an elongated shaft with an axis and a locating end portion for engaging a bony part of the patient. The shaft can include engagement structure, where the engagement structure of the drill jig can engage the engagement structure of the positioning arm crosswise to support the drill guide opening of the drill jig at a location remote from the axis of the elongated shaft. The locating end can include a radiopaque marker. A surgical opening is made, and the locating end is positioned through the surgical opening against the bony part of the patient. The drill jig is attached to the positioning arm, with a portion of the bony part of the patient being positioned between the locating end and the drill guide opening. A drill element is advanced through the drill guide opening and along the drill element guide axis toward the radiopaque marker of the locating end to create a surgical tunnel.

The method can further include an elongated drill guide insert having an elongated open interior drill guide passage for receiving the surgical drill pin or surgical drill element. The drill guide insert can being dimensioned for placement in the drill guide opening of the drill jig, the drill jig and the drill guide insert comprising cooperating securing structure for securing the drill guide insert within the drill guide opening. The method can include the steps of placing a surgical drill pin in the bony part of the patient and then using a surgical drill bit guided by the drill pin to create a surgical tunnel.

The invention includes a method for minimally invasive surgical drilling of the femoral head. The invention can be used for a ligamentum teres reconstruction system, and for an avascular necrosis repair system, among other procedures. The method includes the step of providing an elongated drill jig comprising at an engagement end thereof engagement structure, the drill jig comprising a drill guide opening for defining a location and drill element guide axis for placement of a surgical drill element. A positioning arm can have an elongated shaft with an axis and a locating end portion shaped to engage a part of the femoral head of a patient. The shaft can include engagement structure, where the engagement structure of the drill jig can engage the engagement structure of the positioning arm crosswise to support the drill guide opening of the drill jig at a location remote from the axis of the elongated shaft. A surgical opening is made, and the locating end is positioned through the surgical opening against the femoral head. The drill jig is attached to the positioning arm, with a portion of the femoral head being positioned between the locating end and the drill guide opening. The drill element is advanced through the drill guide opening and along the drill element guide axis toward the locating end to create a femoral tunnel. The locating end can include a radiopaque marker, and the method can further include the step of using a detector to identify the radiopaque marker while advancing the surgical drill element toward the radiopaque marker.

BRIEF DESCRIPTION OF THE DRAWINGS

There are shown in the drawings embodiments that are presently preferred, it being understood that the invention is not limited to the arrangements and instrumentalities shown, wherein.

DETAILED DESCRIPTION OF THE INVENTION

Figure 1:
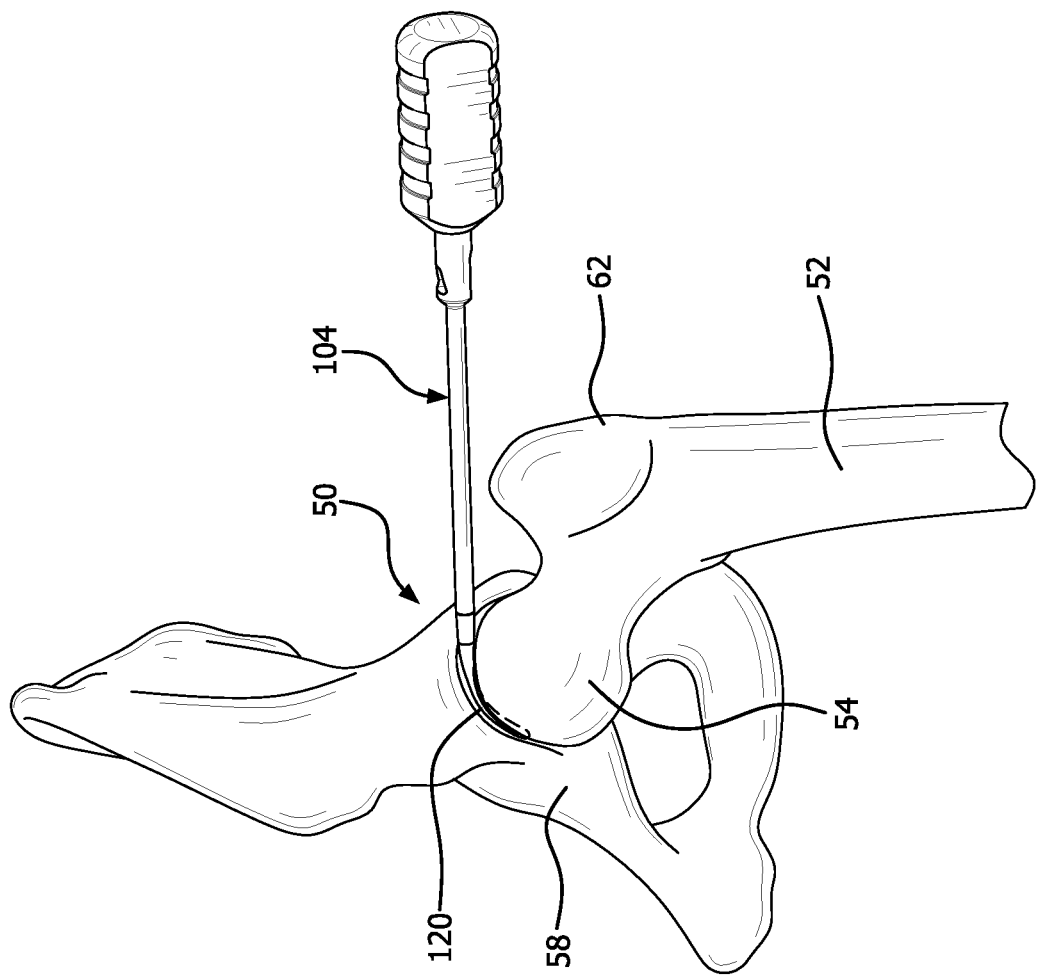
FIG. 1 is a schematic perspective view of a positioning arm according to the invention positioned in part over the femoral head in a hip joint, in a first mode of operation.
Figure 2:
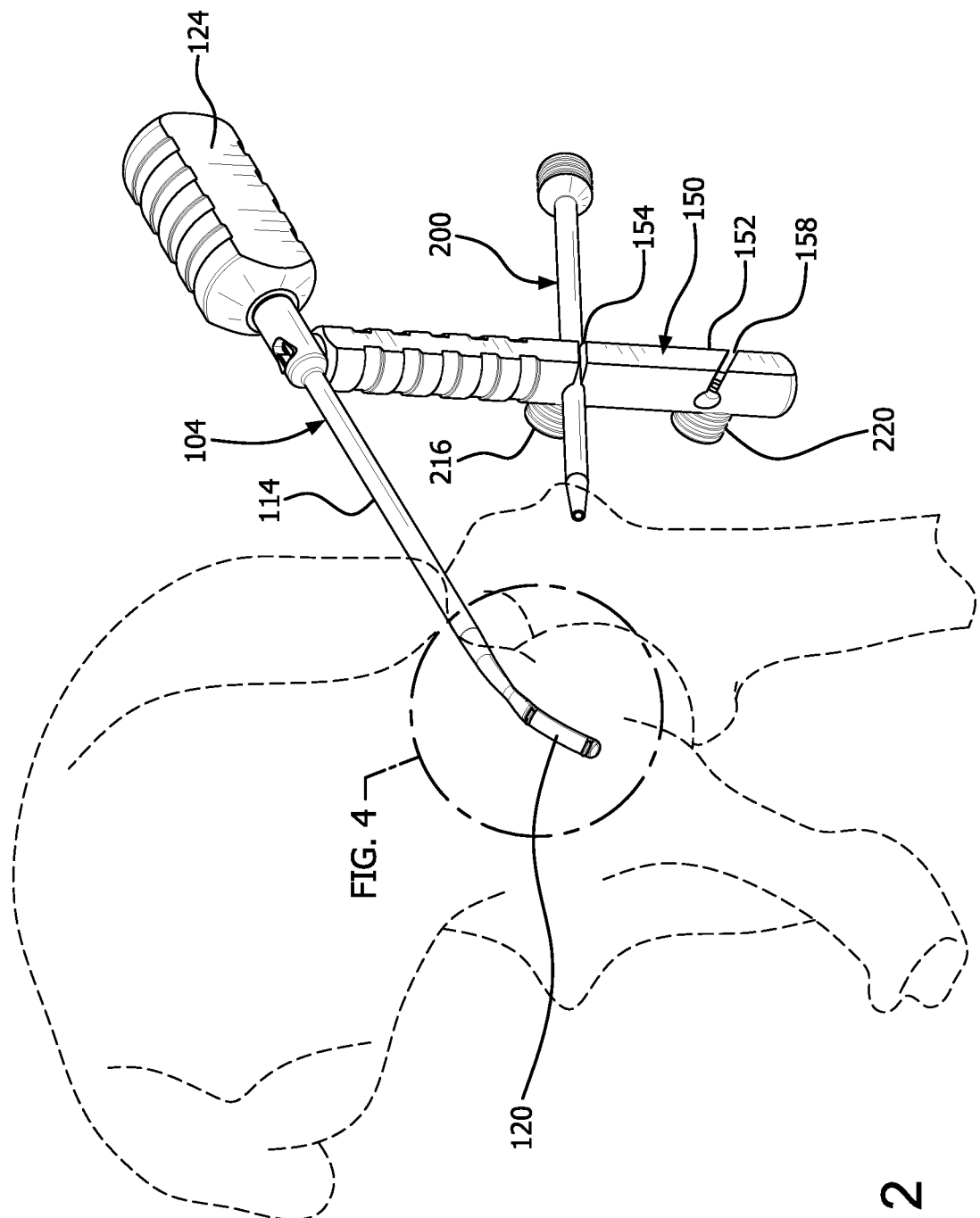
FIG. 2 is a schematic perspective view, partially in phantom, of a drill guide and drill guide insert positioned in part over the femoral head.

A minimally invasive surgical drill guide according to the invention includes an elongated drill jig having at least one drill guide opening for defining a location and drill element guide axis for placement of a surgical drill element. The drill jig can have an engagement end with engagement structure. A positioning arm includes an elongated shaft with a long axis and a locating end portion for engaging a bony part of a patient. The elongated shaft can have engagement structure for engaging to the engagement structure of the drill jig to support the drill jig crosswise relative to the position arm and to support the drill guide opening of the drill jig at a location remote from the axis of the elongated shaft of the positioning arm. The drill jig can be detachable from the positioning arm.

The surgical drill guide can include an elongated removable drill guide insert having an elongated open interior drill guide passage for receiving the surgical drill element. The drill guide insert can be dimensioned for placement in the drill guide opening of the drill jig. The drill jig and/or the drill guide insert can have suitable securing structure for securing the drill guide insert within the drill guide opening. The interior drill guide passage can be dimensioned for a surgical drill guide pin, surgical drill bit, or other suitable drill element.

The drill guide opening can include a channel having a drill element guide axis aligned with the locating end. When a surgical drill element is advanced through the drill guide opening, the drill element will advance along the drill element guide axis toward the locating end. The elongated drill guide insert when secured in the drill guide opening will also guide the drill element along the drill guide axis toward the locating end.

The locating end can have varying sizes and shapes. In one embodiment, the locating end is shaped to mate with a bony part of the patient. The locating end can be curved. The curved locating end can be configured to mate with a portion of the femoral head. The curved locating end can be configured to mate with the fovea. The surgeon will thereby be able to conduct the procedure from a known point of reference. Also, the fovea serves as the attachment point for the ligamentum teres, and so this is an appropriate location for the ligamentum teres reconstruction procedure.

Minimally invasive procedures require proper location and alignment of the surgical drill element, which are out of the direct view of the surgeon. It is common for the surgeon to utilize visualization aids such as fluoroscopes to guide the procedure, however, even with the use of such devices it can be challenging to properly direct the surgical drill element. The surgical drill guide of the invention can provide the locating end with one or more a radiopaque markers. The radiopaque markers will be visible to the fluoroscope or other detector, and will provide a distinctive shape or appearance that permits the surgeon to identify the marker and its location and properly position and align the drill guide. The radiopaque marker can include a raised radiopaque protrusion. The raised protrusion comprises at least one radiopaque ridge. The drill guide openings of the elongated drill jig can provide a drill element guide axis that is directed toward a radiopaque marker associated with each drill guide opening. The drill element guide axis of each drill guide opening intercepts the associated radiopaque marker. The surgeon can thereby visualize the drill element as it advances toward the locating end and the radiopaque marker.

The elongated drill jig can have differing shapes and dimensions. The drill jig can have a long axis, and the drill element guide axis can be from 35 to 45 degrees from a normal to the elongated drill jig axis. This is appropriate for an avascular necrosis repair procedure. The drill element guide axis can be from 15 to 30 degrees from a normal to the drill jig axis for a ligamentum teres reconstruction procedures. Other orientations of the drill element guide axis are possible for other procedures, or for different patients and surgical protocols. The drill jig can have multiple drill guide openings for multiple different procedures. The drill jig can include drill guide openings for both the ligamentum teres reconstruction procedure, and for the avascular necrosis repair procedure.

A method for minimally invasive surgical drilling, such as the drilling of the femoral head, can include the steps of providing an elongated drill jig comprising at an engagement end thereof engagement structure. The drill jig comprises a drill guide opening for defining a location and drill element guide axis for placement of a surgical drill element. A positioning arm having an elongated shaft with an axis and a locating end portion shaped is configured to engage a part of the femoral head or other bony part of a patient. The shaft can include engagement structure. The engagement structure of the drill jig engages the engagement structure of the positioning arm crosswise to support the drill guide opening of the drill jig at a location remote from the axis of the elongated shaft. A surgical opening is made and the locating end is positioned through the surgical opening against the femoral head or other bony part of the patient. The drill jig is attached to the positioning arm, with a portion of the femoral head or other bony part being positioned between the locating end and the drill guide opening. A drill element such as a surgical pin is advanced through the drill guide opening and along the drill element guide axis toward the locating end to create a femoral tunnel. The locating end can include a radiopaque marker. The drill element can be advanced through the drill guide opening and along the drill element guide axis toward the radiopaque marker of the locating end. The method can further include the step of using a detector such as a fluoroscope to identify the radiopaque marker while advancing the surgical drill element toward the radiopaque marker. A surgical drill bit can then be used and guided by the surgical drill pin to create a repair tunnel.

The drill guide can include an elongated drill guide insert having an elongated open interior drill guide passage for receiving the surgical drill pin. The drill guide insert can be dimensioned for placement in the drill guide opening of the drill jig. The drill jig and the drill guide insert can include cooperating securing structure for securing the drill guide insert within the drill guide opening. The method can include the steps of placing the drill guide insert into the drill guide opening of the drill jig and securing it in position. The drill pin can then be placed in the drill guide insert, and advanced through the femoral head. A surgical drill bit can be guided by the drill pin to create the femoral tunnel. The method can include the step of using the femoral tunnel to connect a ligamentum teres repair device to the acetabulum of the patient. The method can include the step of placing a reconstructive material into the femoral tunnel for avascular necrosis repair.

There is shown in the figures a hip joint 50 including femur 52, femur head to 54, greater trochanter 56, and acetabulum 58. The invention will be described in the context of two common procedures undertaken at the hip joint, the ligamentum teres reconstruction and the avascular necrosis repair procedures, however, the invention has utility for other procedures and in alternative locations to the hip joint. The drill guide assembly 100 includes a positioning arm 104, and elongated drill jig 150, and can include a removable drill guide 200.

The positioning arm 104 includes an elongated shaft 114 having a long axis, a locating end 120, and the handle 124. The handle 124 can be fixed to the elongated shaft 114, or can be removable. The locating end 120 can include a surface 130 that can be configured to mate with a bony part of the patient such as the femoral head 54. It will be appreciated that the locating end 120 can be configured to mate with other bony parts of a patient depending on the procedure that will be performed. The locating end 120 serves to identify the location and alignment of and secure the positioning arm 104 for the procedure and to help to secure the positioning arm in position during the procedure. The locating end 120 can have radiopaque markers which can be protrusions or other structure which is visible by suitable detectors such as fluoroscopes or other devices. The protrusions can be in differing shapes and sizes. The protrusions can be in the form of ridges 128. One or more protrusions can be provided for properly locating different procedures. The ridges 128 can be provided for properly directing a surgical drill element for a ligamentum teres reconstruction procedure. Another set of ridges 132 can be provided for properly directing a surgical drill element for an avascular necrosis repair procedure. More or fewer protrusions can be provided for more or fewer procedures, and the protrusions can be located elsewhere on the locating end 120 for differing procedures.

Figure 3:
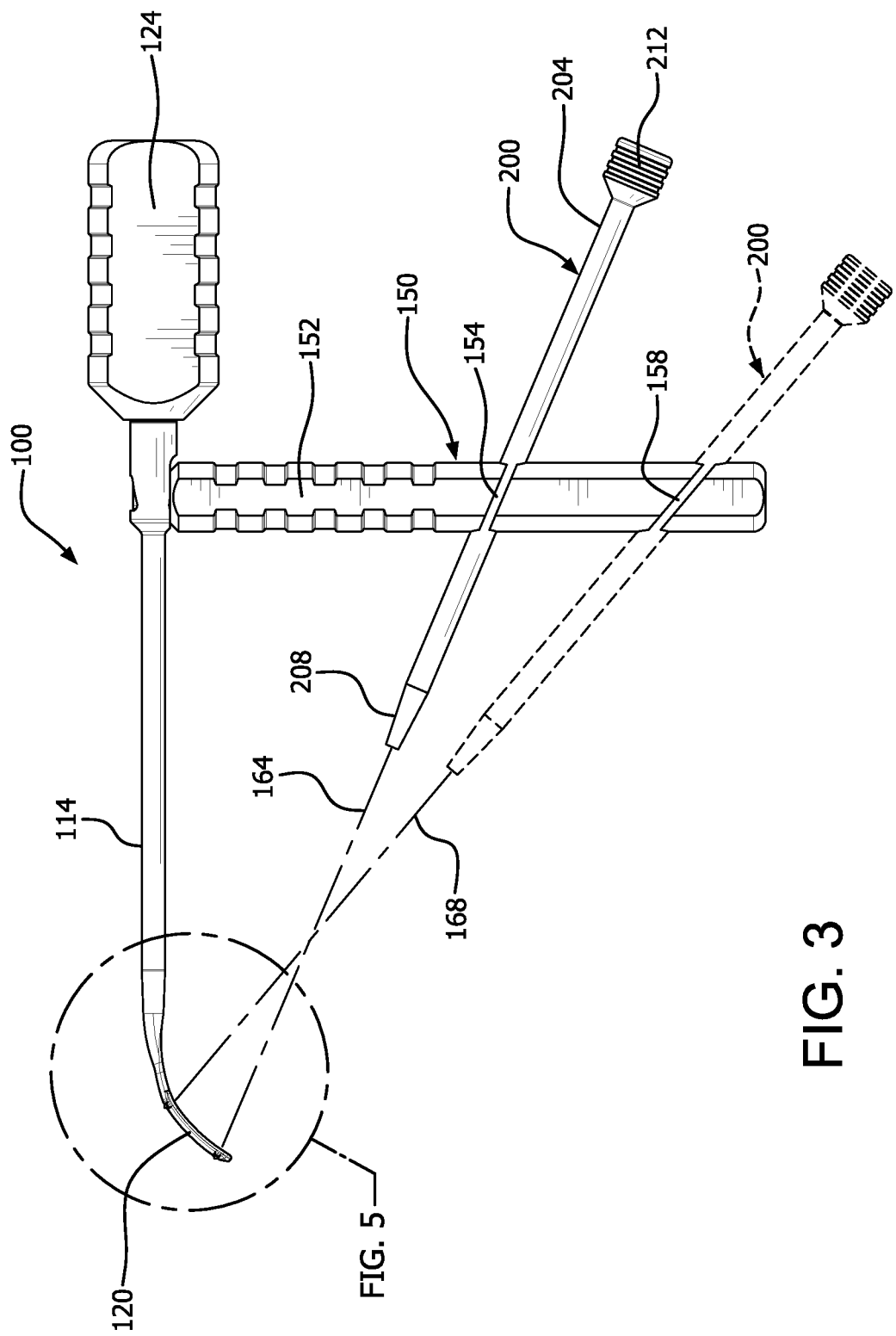
FIG. 3 is a schematic side elevation, partially in phantom, of a drill guide and drill guide insert.
Figure 4:
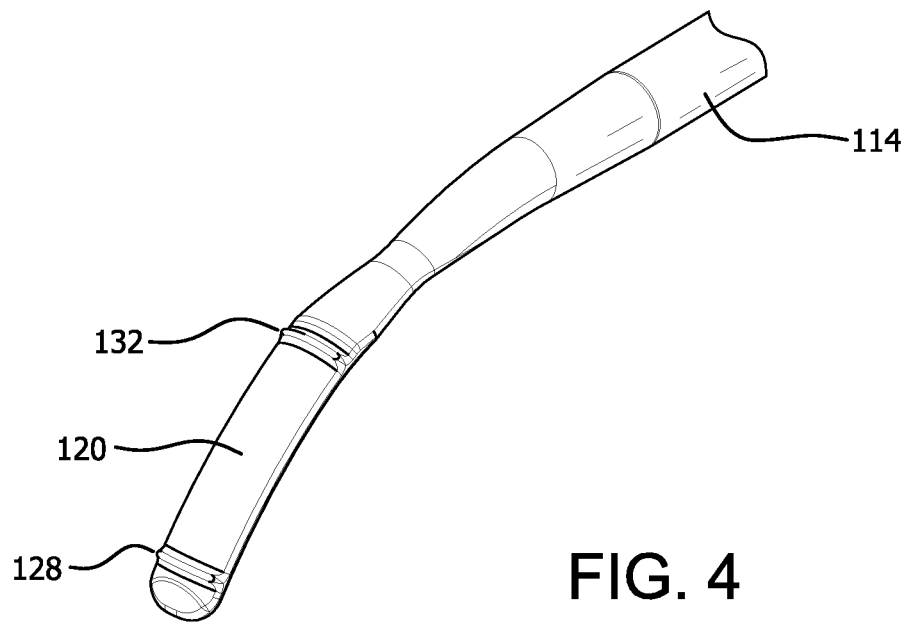
FIG. 4 is an expanded perspective view of a locating end of the positioning arm.
Figure 5:
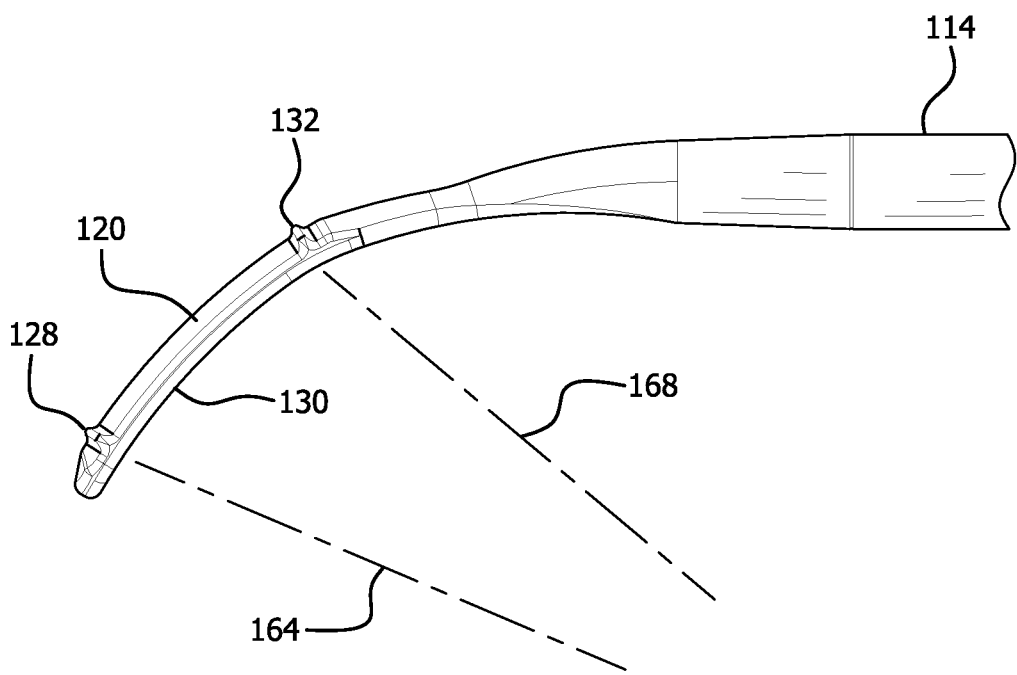
FIG. 5 is an exploded side elevation of area FIG. 5 in FIG. 3.

The drill jig 150 is connectable to the positioning arm 104. The drill jig 150 includes an elongated body 152 comprising one or more drill guide openings such as the drill guide openings 154 and 158. The drill guide openings serve to direct the surgical drill element such as the surgical pin or surgical drill bit for the specific procedure that is being performed. The drill guide opening will therefore be located and angled differently for different procedures. In the embodiment shown, drill guide opening 154 is provided for a ligamentum teres reconstruction procedure, and drill guide opening 158 is provided for an avascular necrosis repair procedure (FIG. 3). The drill guide opening 154 can for example define a drill element guide axis 164 that is appropriately directed for a surgical tunnel for a ligamentum teres repair procedure. The drill guide opening 158 can define a drill element guide axis 168 that is appropriately directed for a surgical tunnel for a avascular necrosis repair procedure. The surgical drill element will be guided by the drill guide opening location and direction relative to the position of the locating end 120. The drill element guide axis 164 can for example a line with protrusion 128 such that with an appropriate detection method such as fluoroscopy, the surgeon can visualize the proper advance of the surgical drill element to the appropriate location relative to the femoral head 54 for a ligamentum teres reconstruction procedure (FIG. 5). Similarly the drill element guide axis 168 can align with the protrusion 132 such that the surgeon can visualize the proper advance of the surgical drill element to the appropriate location relative to the femoral head 54 for an avascular necrosis repair procedure.

Figure 6:
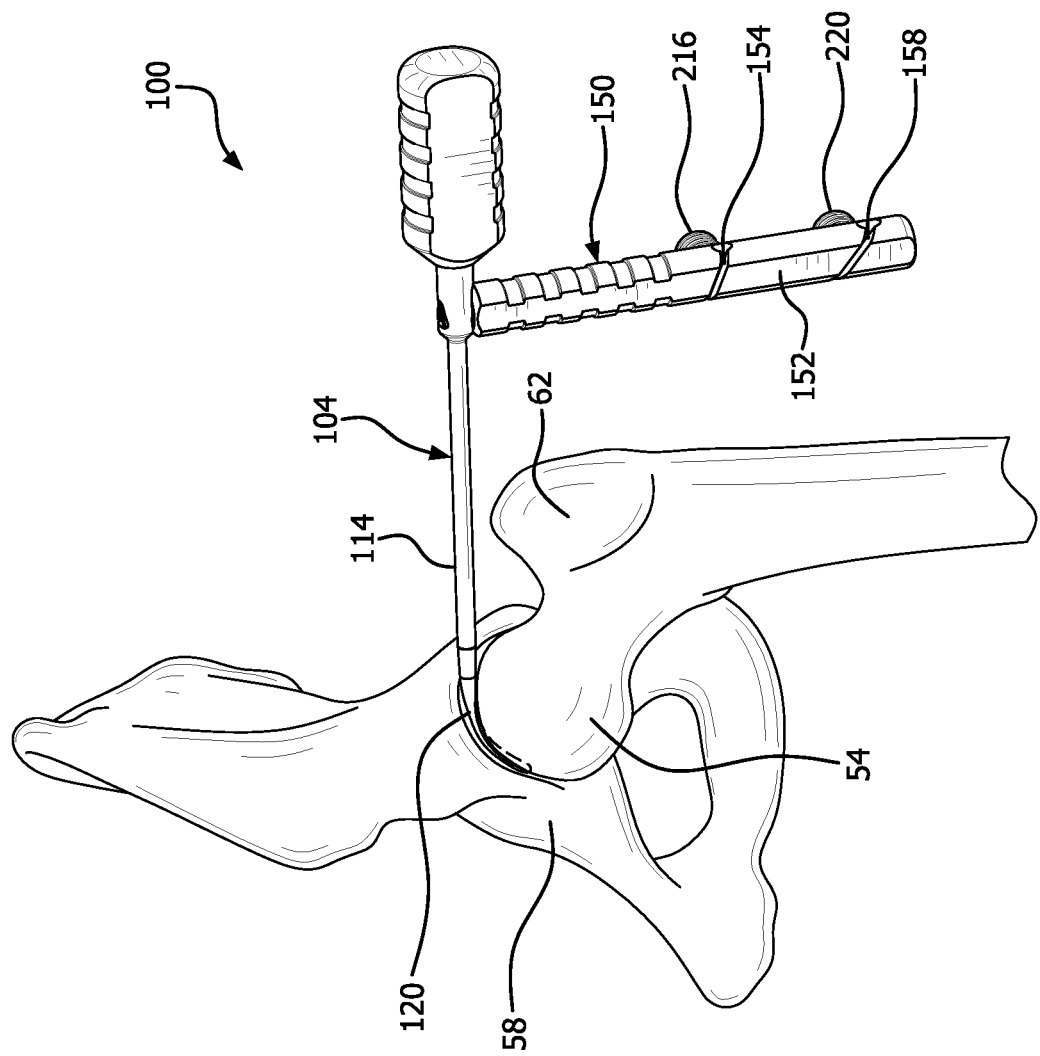
FIG. 6 is a schematic perspective view of a drill guide in the hip joint in a second mode of operation.

The procedure begins with insertion of the positioning arm 104 through a proper minimally invasive surgical opening. The locating end 120 is positioned over the femoral head 54 (FIG. 1). The drill jig 150 is then secured to the positioning arm 104 (FIG. 6). The manner of attachment can vary. The drill jig 150 is attached end wise to the positioning arm 104 at an engagement end 170. A lateral end 180 is distal to the axis of the elongated shaft 114 such that the drill guide openings 154 and 158 will be remote from the axis of the elongated shaft 114, and properly positioned for the respective surgical procedure.

Figure 7:
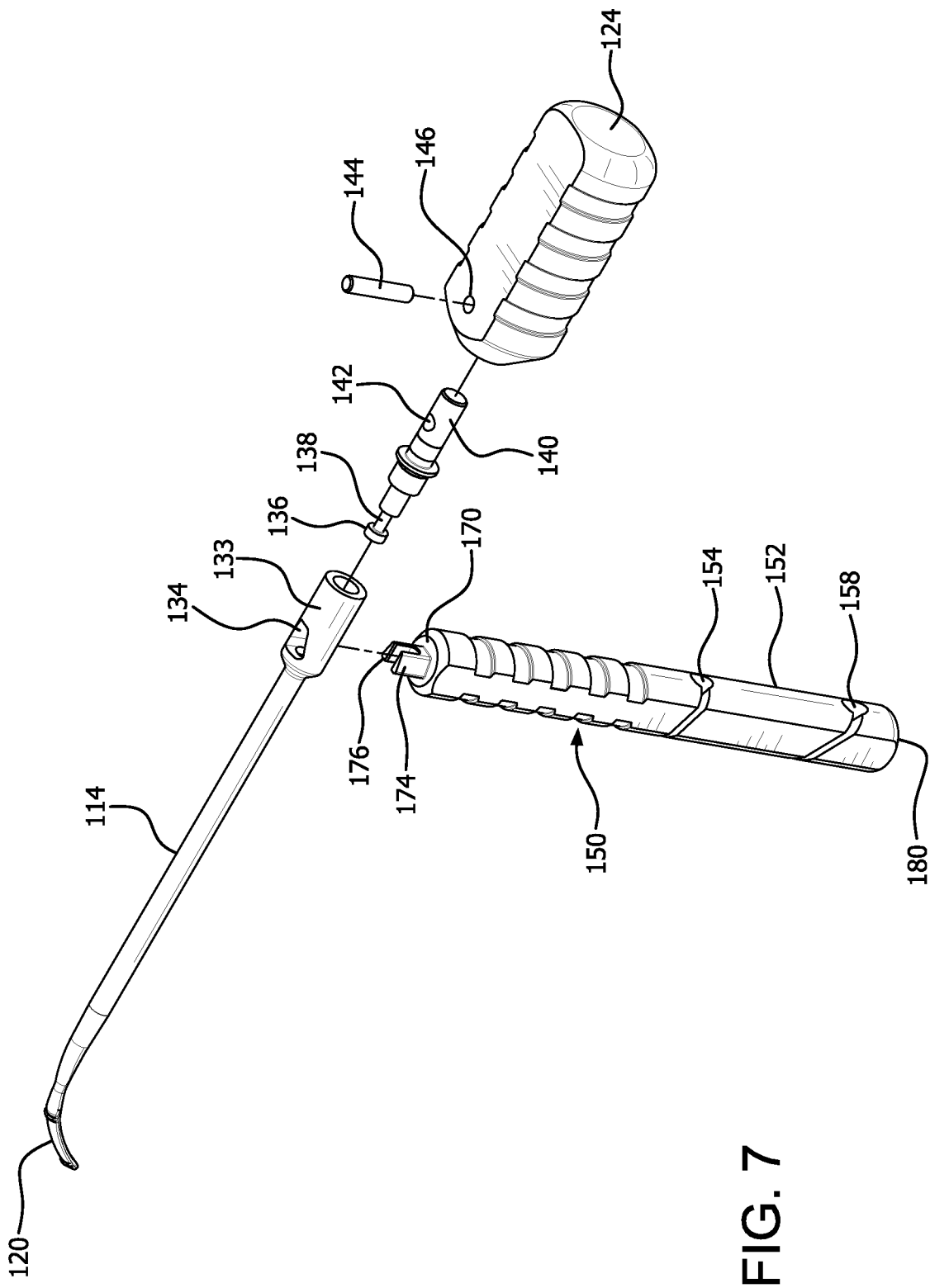
FIG. 7 is an exploded perspective of the drill guide.

The manner of attachment of the drill jig 152 to the positioning arm 104 can vary. The drill jig 150 is attached crosswise to the elongated shaft 114 such that the drill guide openings 154 and 158 will be suspended laterally outward from the axis of the elongated shaft 114 and properly positioned for the surgical procedure. The drill jig 150 is preferably detachable from the positioning arm 104. Snap fitting projections 174, 176 can be provided at the engagement and 170 of the drill jig body 152 (FIG. 7). An engagement body 133 can be provided at a proximal and of the elongated shaft 114 and can have an engagement opening 134 for receiving the snap fitting projections 174, 176. An engagement fitting 140 is adapted for insertion into the engagement body 133 of the positioning arm 104 and can be fixed in position by engagement seat 136. The snap fitting projections 174, 176 when inserted into the engagement opening 134 provide for a snap-fit engagement to cylinder 138 of fitting 140. An aperture 142 is adapted to receive securing pin 144 placed through opening 146 in handle 124 to secure the assembly together. Other constructions are possible.

Figure 8:
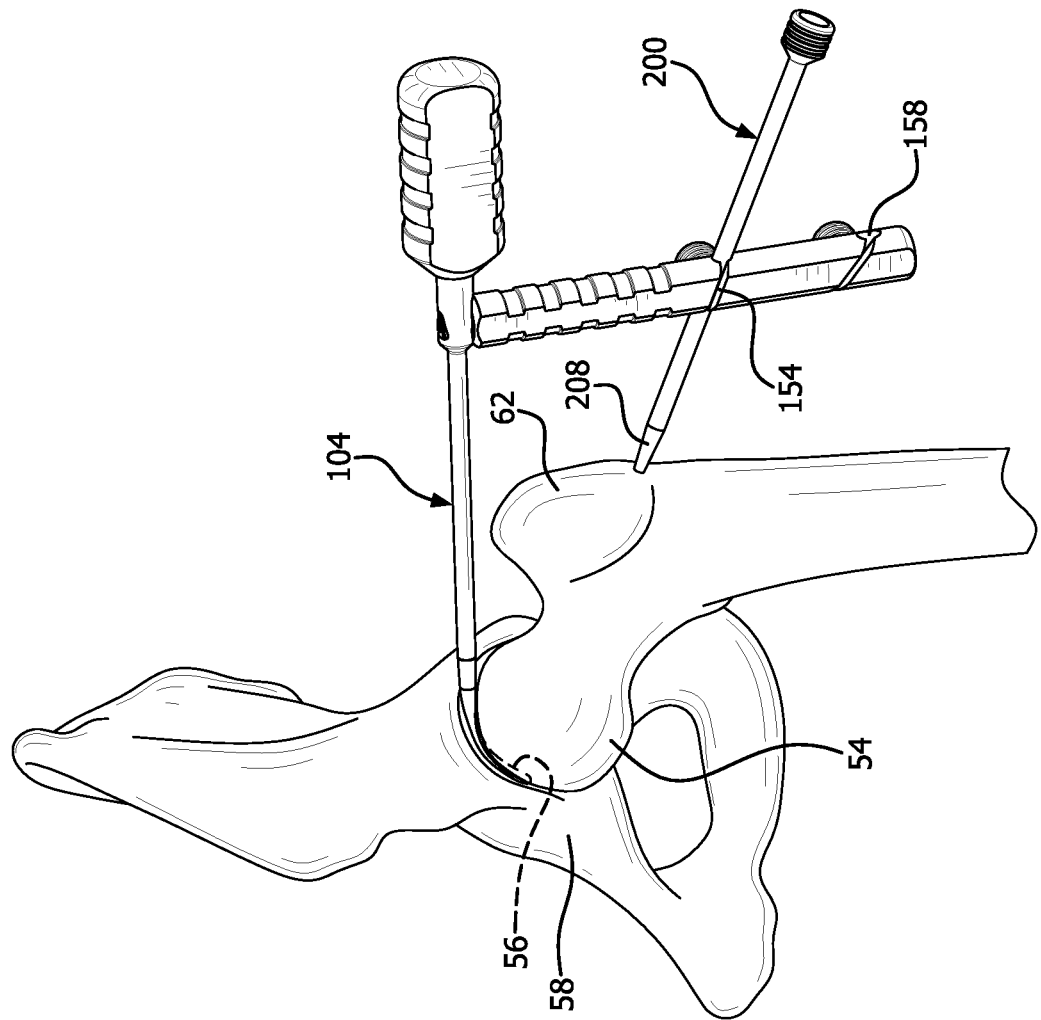
FIG. 8 is a schematic perspective of a drill guide and drill guide insert in the hip joint in a third mode of operation.
Figure 9:
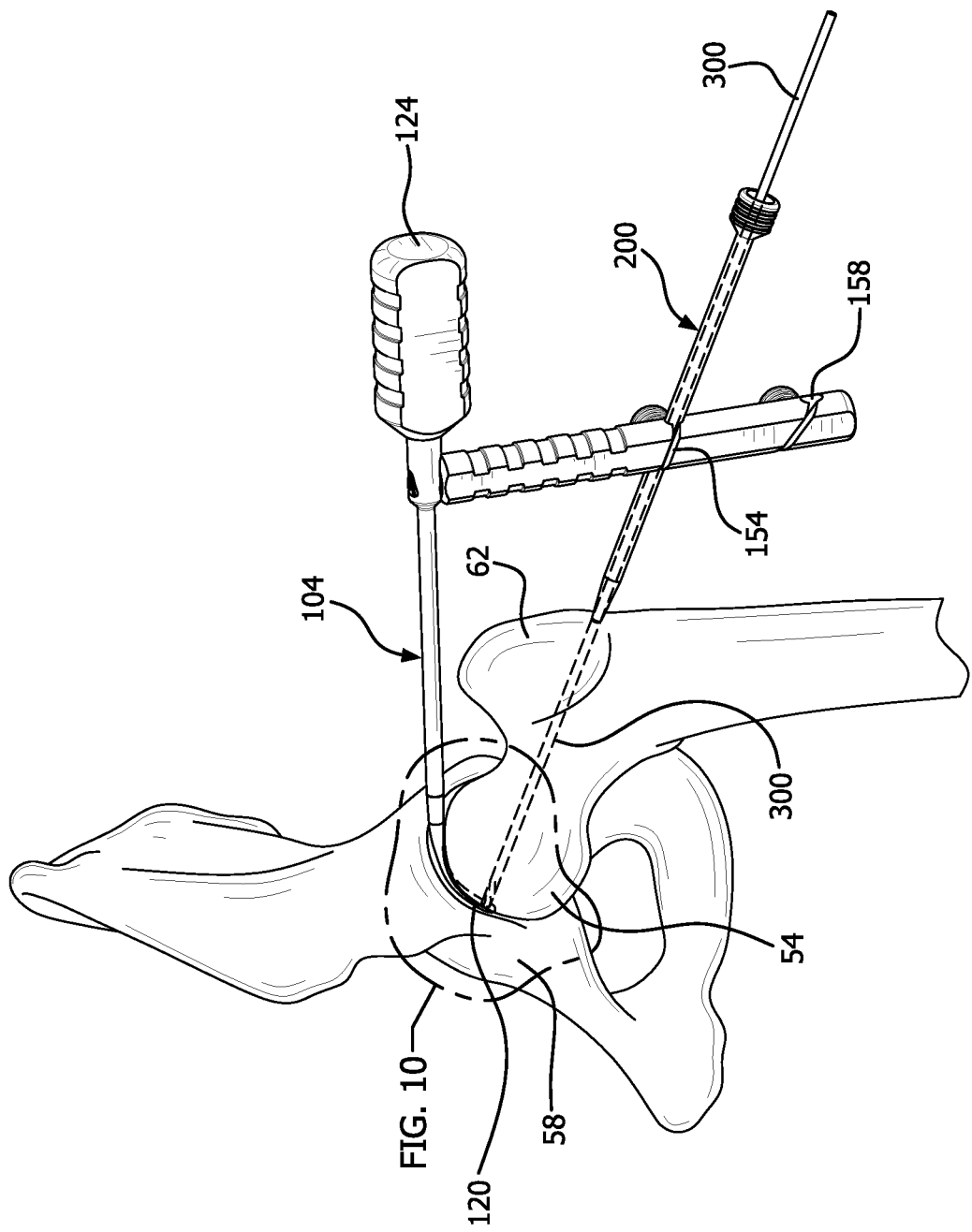
FIG. 9 is a schematic perspective, partially in phantom, view of a drill guide and drill guide insert in the hip joint in a fourth mode of operation and using a surgical drill pin.

The drill guide openings 154 and 158 in the drill jig body 152 can themselves serve as a guide for the surgical drill element. Additional drill guide structure can be fixed to the drill jig body 152 about the drill guide opening to support and direct the surgical drill element. It is preferable however to provide an elongated removable drill guide insert 200 that is insertable into the drill guide openings 154 and 158 (FIG. 8). Different patients and procedures will require different, and differently sized, surgical drill elements such as surgical pins. A removable drill guide insert 200 permits the replacement of the drill guide insert for the diameter of the surgical drill element that is necessary for the particular patient and procedure. The drill guide insert 200 can be tubular and comprise a locating tip 208 and a threaded head 212. A central bore through the drill guide insert 200 permits the drill guide insert to accept the surgical drill pin 300 (FIG. 9). Securing structures such as set screws with tightening knobs 216 and 220 can be provided to secure the drill guide insert 200 in the drill guide opening 154 and 158, respectively. Other securing structure is possible.

Figure 10:
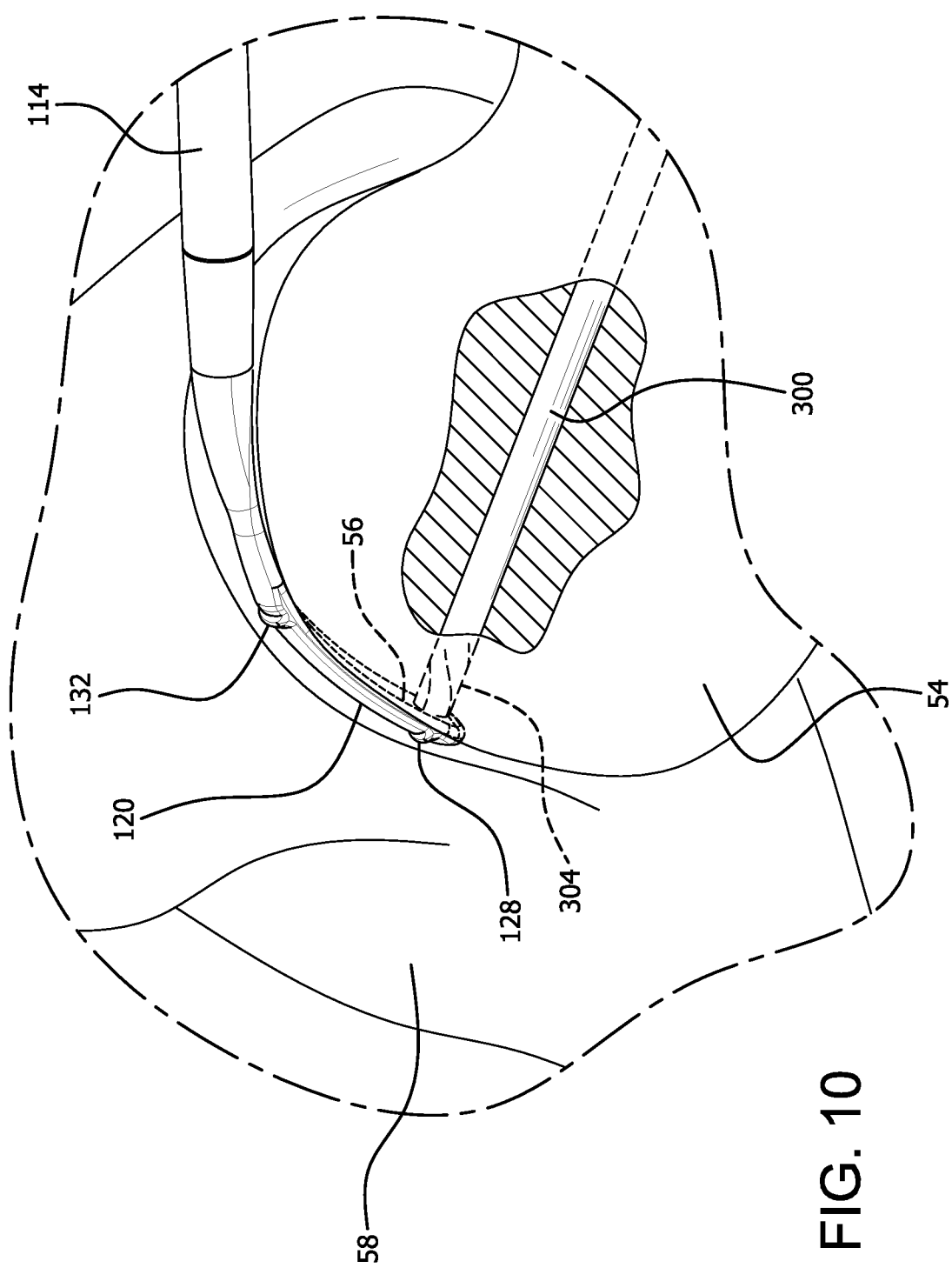
FIG. 10 is an enlarged perspective view of area FIG. 10 in FIG. 9, partially in phantom and partially broken away.

It is common in orthopedic procedures to place a surgical pin as an initial surgical drill element, and to verify the proper placement of the surgical pin prior to drilling a surgical tunnel, which can be several millimeters in diameter. The invention facilitates this process with the use of the locating end 120 and radiopaque markers such as protrusions 128 and 132. As shown in FIG. 10, the surgical pin 300 can be advanced in a ligamentum teres reconstruction procedure until the tip 304 has advanced to the appropriate guide marker protrusion 128. This is visualized by the surgeon using fluoroscopy or similar technology throughout the procedure. Additionally, because the locating end 120 can be mated with landmark structures such as fovea 56, accurate placement of the surgical pin 300 is facilitated.

Figure 11:
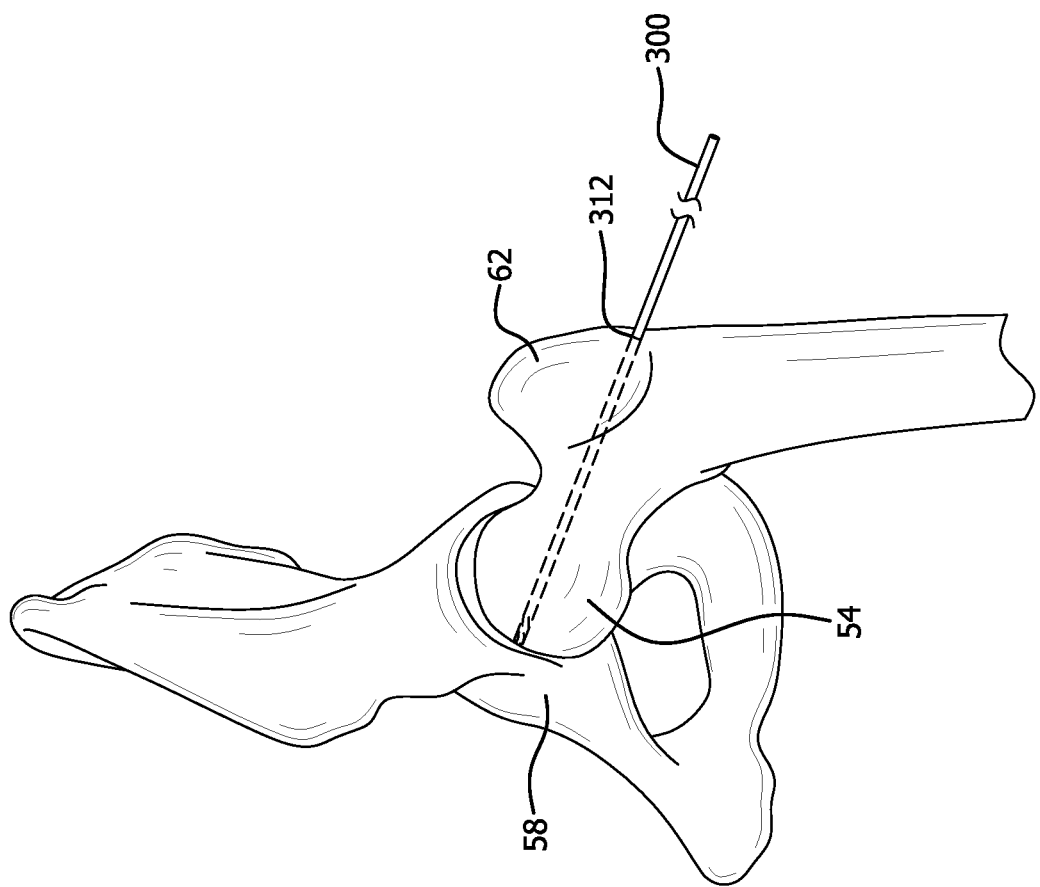
FIG. 11 is a schematic perspective view of a surgical pin in a hip joint, partially in phantom, as part of a ligamentum teres reconstruction procedure.
Figure 12:
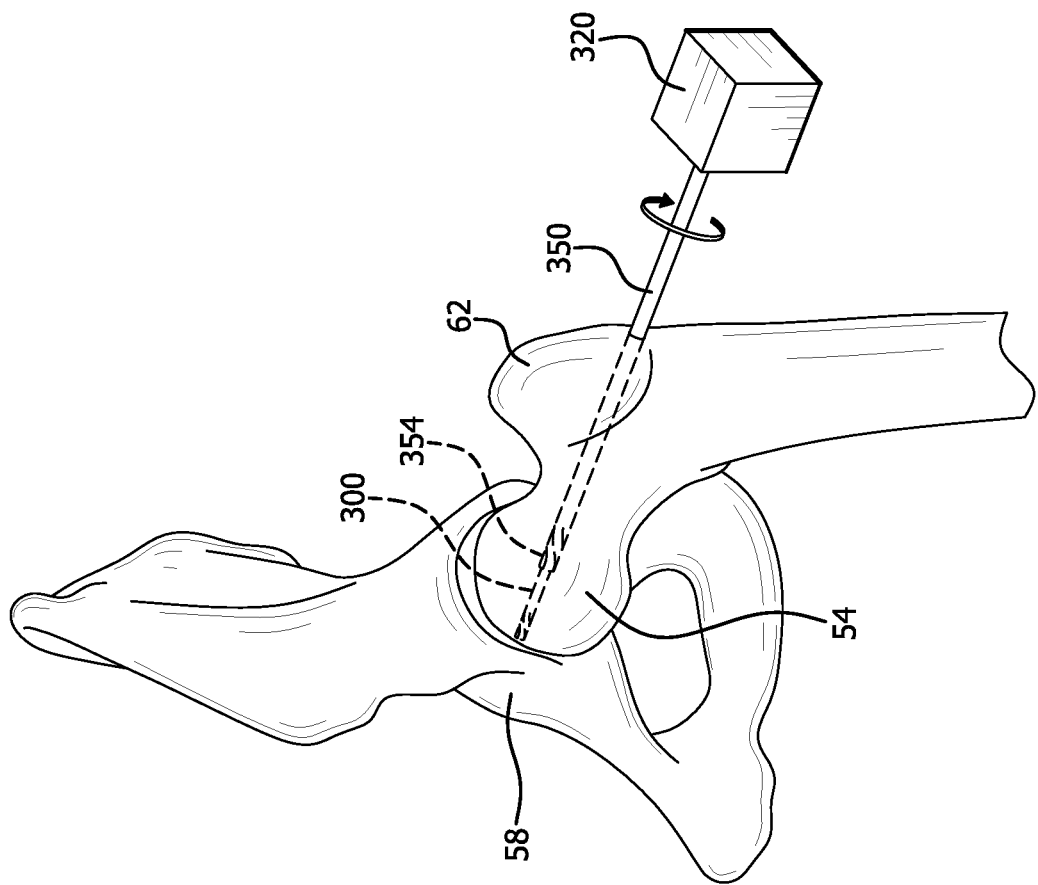
FIG. 12 is a schematic perspective view, partially in phantom, of a surgical drill in use in a hip joint as part of a ligamentum teres reconstruction procedure.
Figure 13:
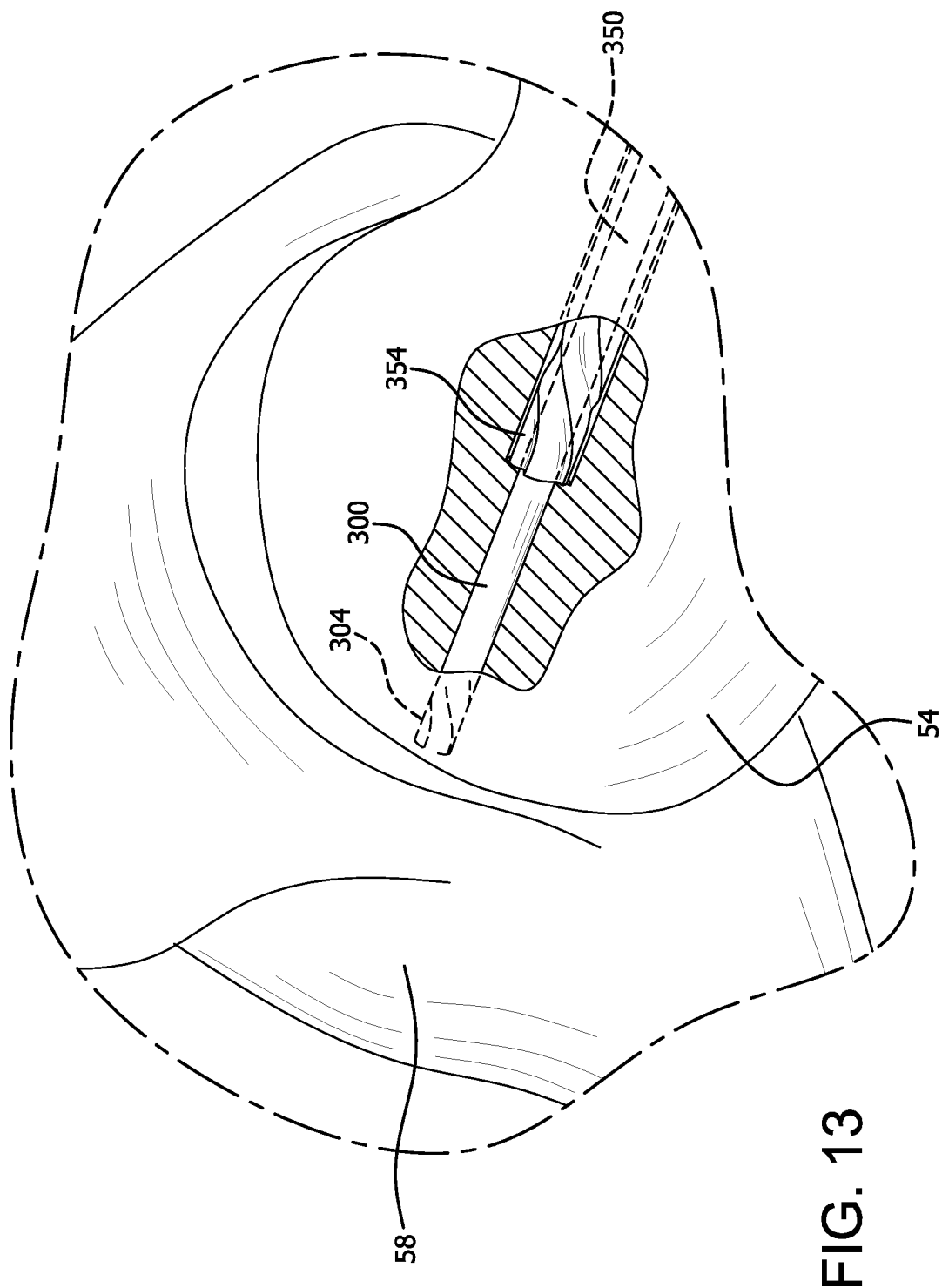
FIG. 13 is an enlarged perspective view, partially in phantom and partially broken away, of a surgical drill in use in a hip joint as part of a ligamentum teres reconstruction procedure.
Figure 14:
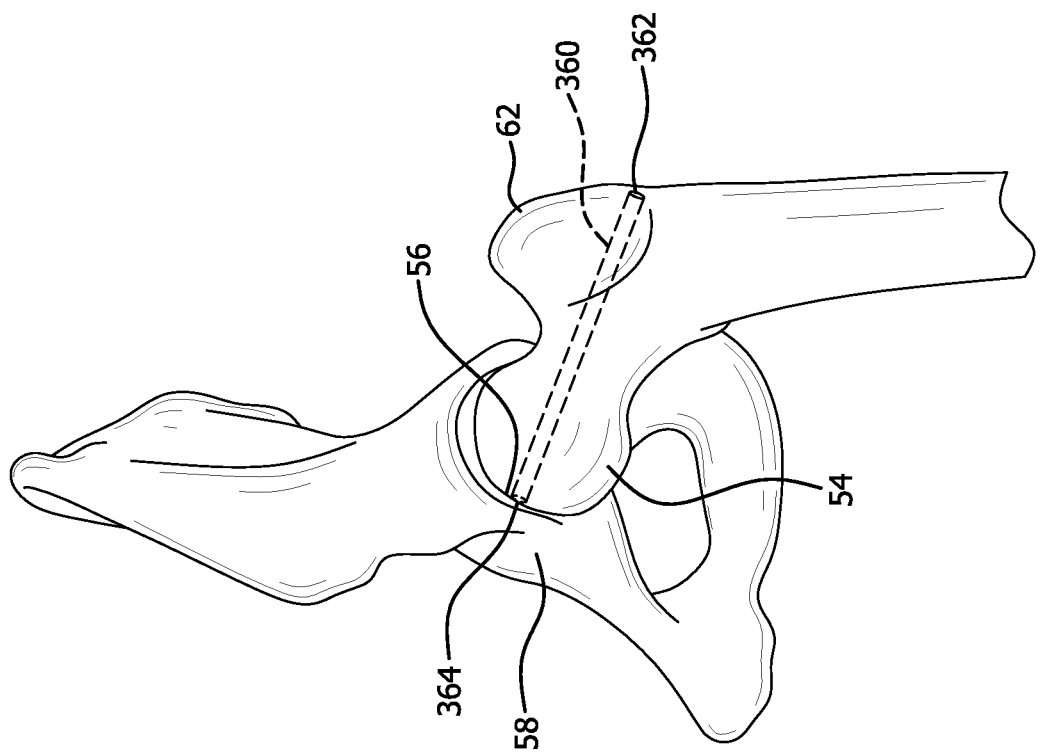
FIG. 14 is a schematic perspective view, partially in phantom, of a surgical tunnel in a hip joint as part of a ligamentum teres reconstruction procedure.

The surgeon will verify that the surgical pin 300 has been placed at an inappropriate opening 312 made in the greater trochanter 62. The drill guide assembly 100 can then be removed (FIG. 11). The surgical pin 300 is then used as a guide as known in orthopedic procedures for surgical drill 320 and drill bit 350. The drill bit 350 has a central bore which receives the surgical pin 300 and allows the surgical drill bit 350 to be advanced with the surgical drill pin 300 guiding the surgical drill bit 350 (FIG. 12). The surgical drill bit 350 is advanced until the tip 354 of the surgical drill bit is advanced to the tip 304 of the surgical pin 300 (FIG. 13). The surgical pin 300 and drill bit 350 can be removed leaving an appropriate surgical tunnel 360 with an opening 362 at the greater trochanter 62 and an opening 364 at the acetabulum 58.

Figure 15:
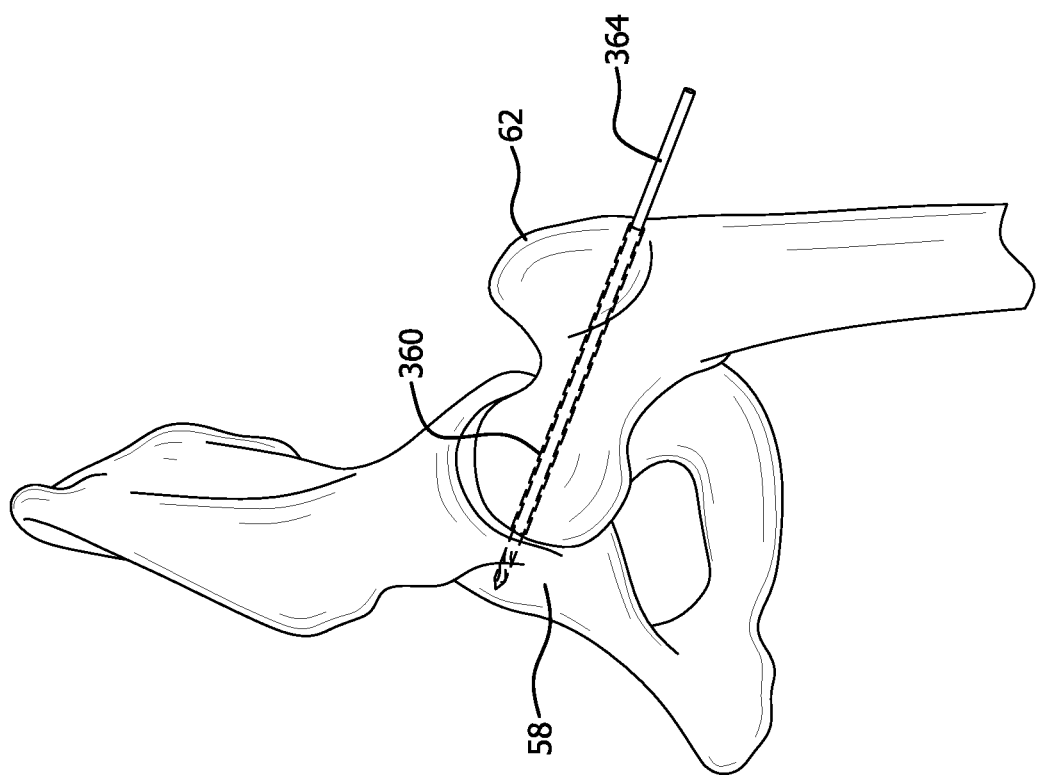
FIG. 15 is a schematic perspective view, partially in phantom, of a surgical drilling procedure through the acetabulum.
Figure 16:
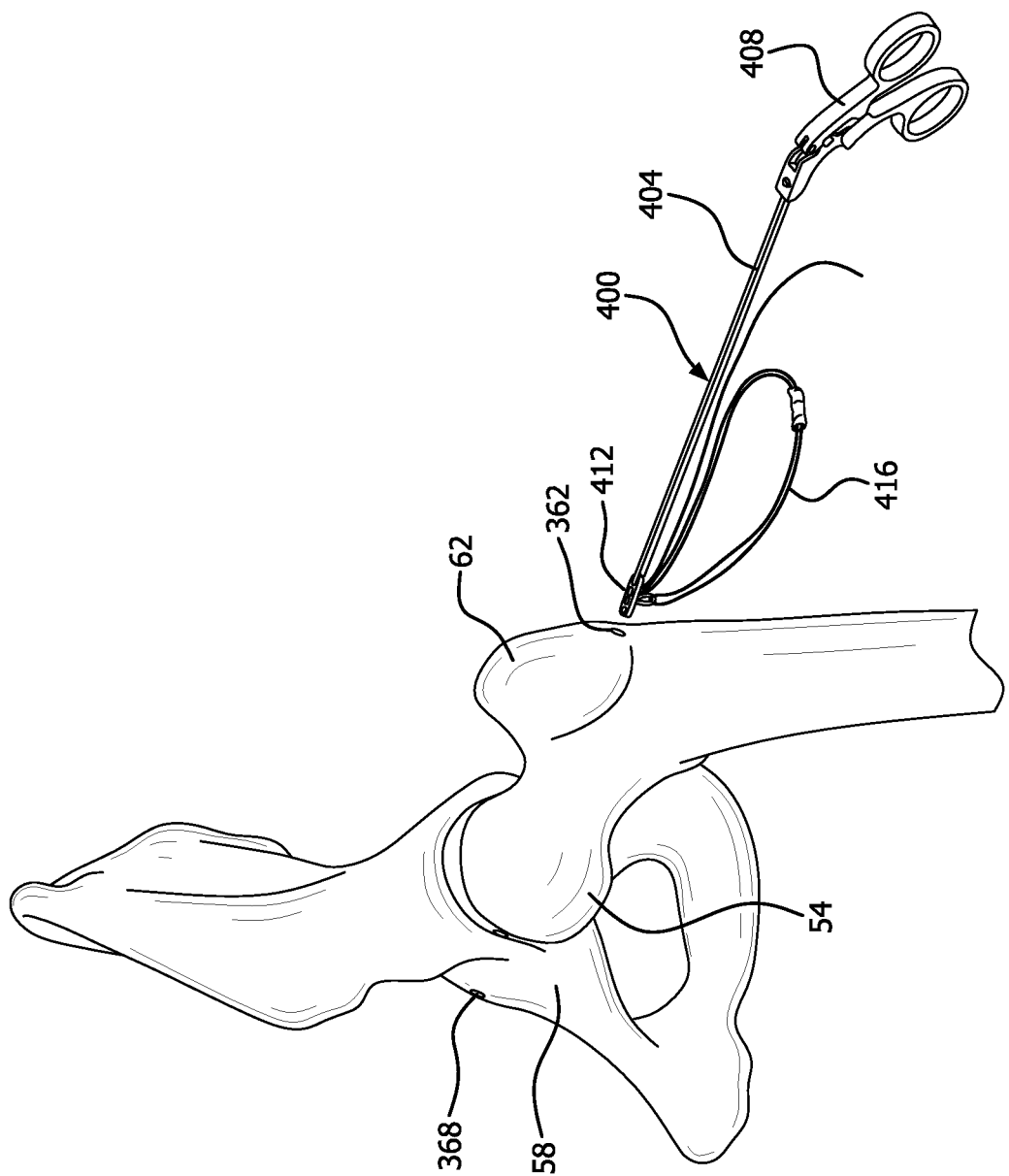
FIG. 16 is a schematic perspective view of a first step of a button insertion procedure through a surgical tunnel in the hip joint as part of a ligamentum teres reconstruction procedure.
Figure 17:
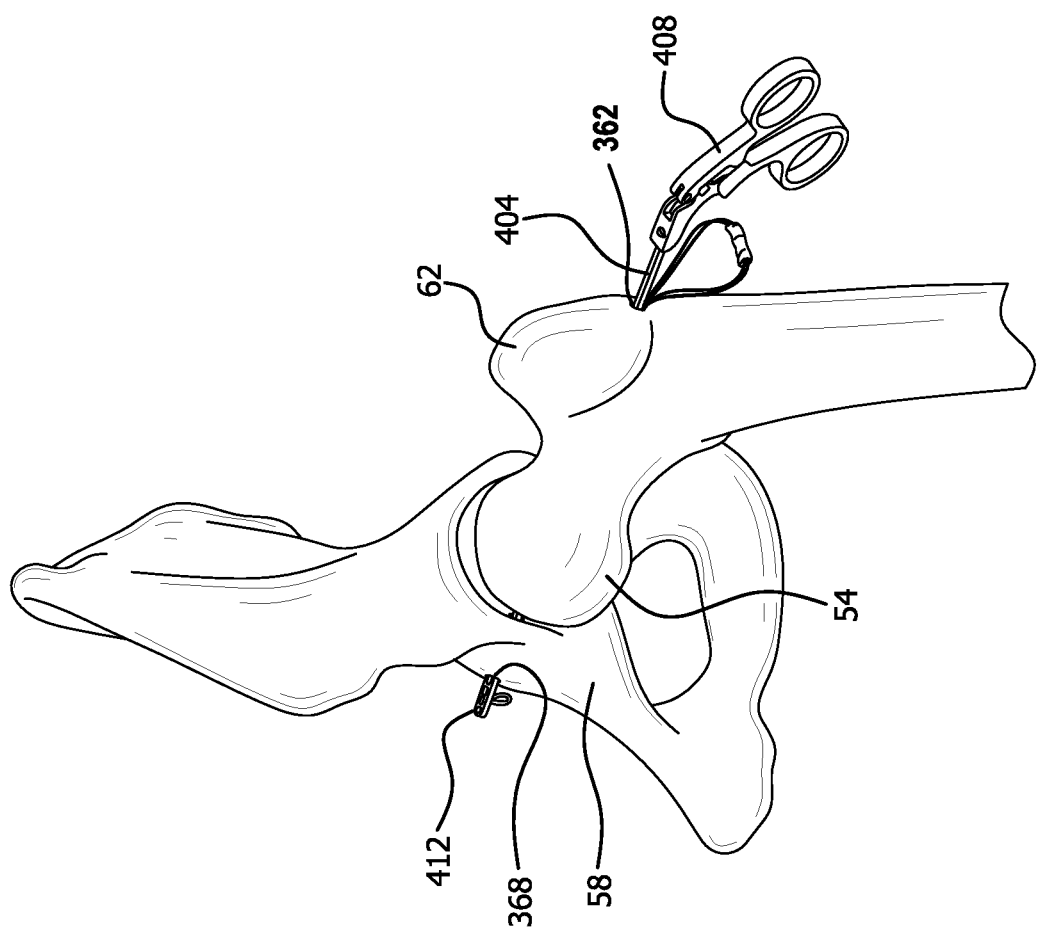
FIG. 17 is a schematic perspective view of a second step of a button insertion procedure through a surgical tunnel in the hip joint as part of a ligamentum teres reconstruction procedure.
Figure 18:
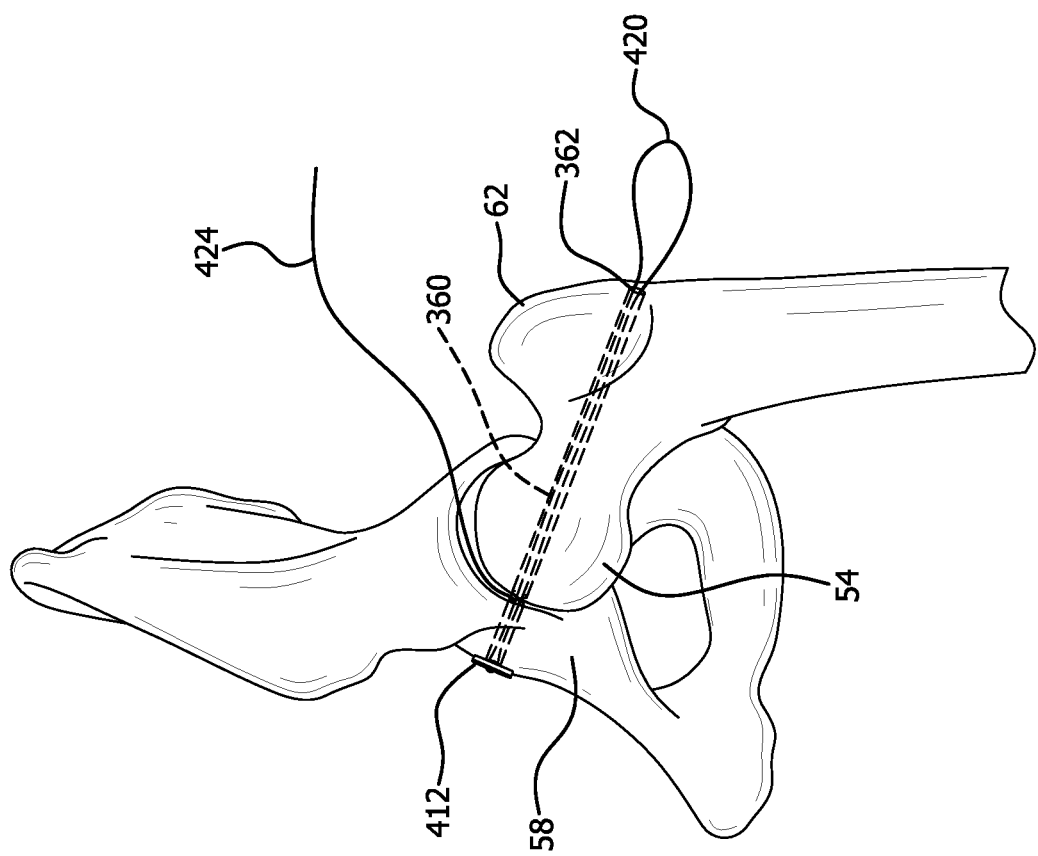
FIG. 18 is a schematic perspective view, partially in phantom, of a third step of a button insertion procedure through a surgical tunnel in the hip joint as part of a ligamentum teres reconstruction procedure.
Figure 19:
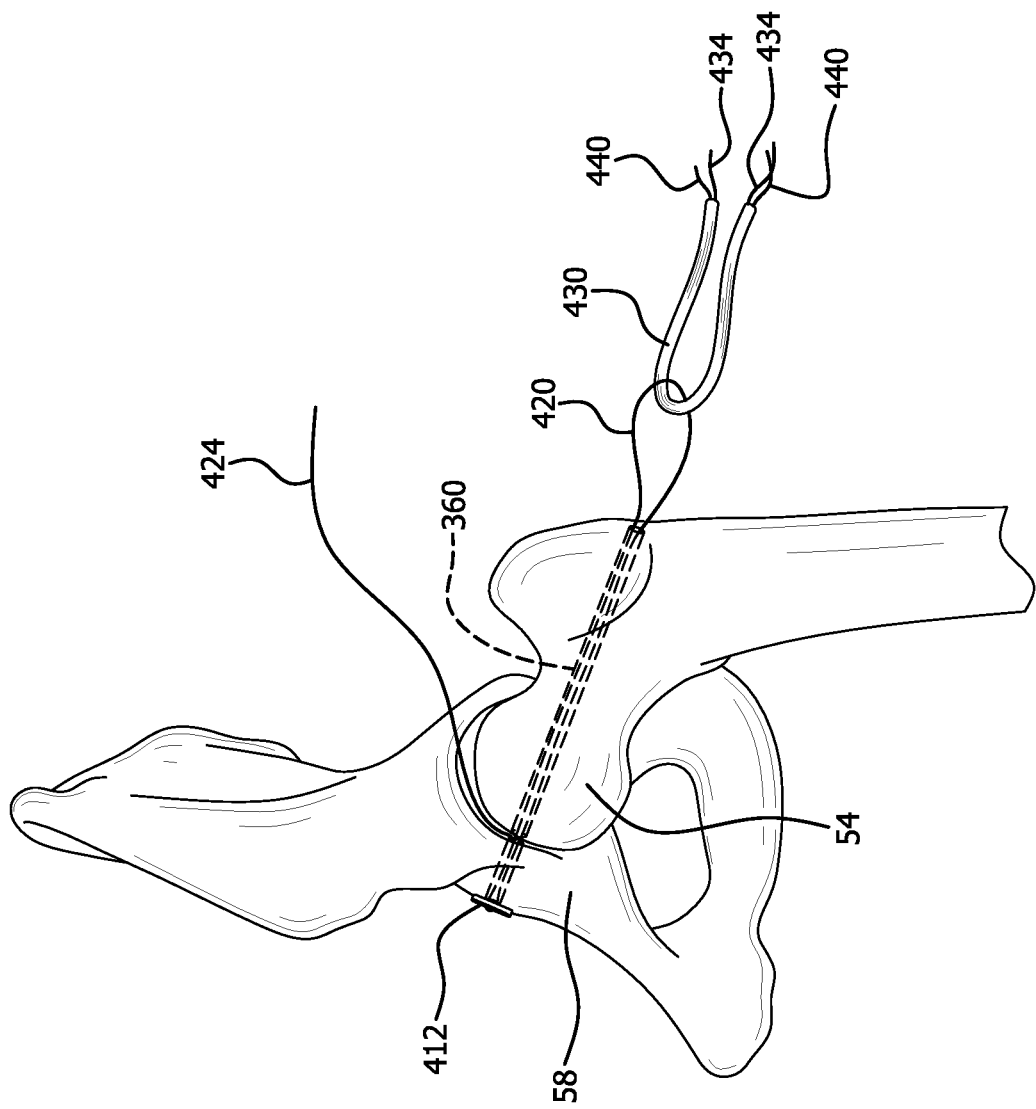
FIG. 19 is a schematic perspective view, partially in phantom, of a first step of a graft insertion procedure through surgical tunnel in the hip joint as part of a ligamentum teres reconstruction procedure.
Figure 20:
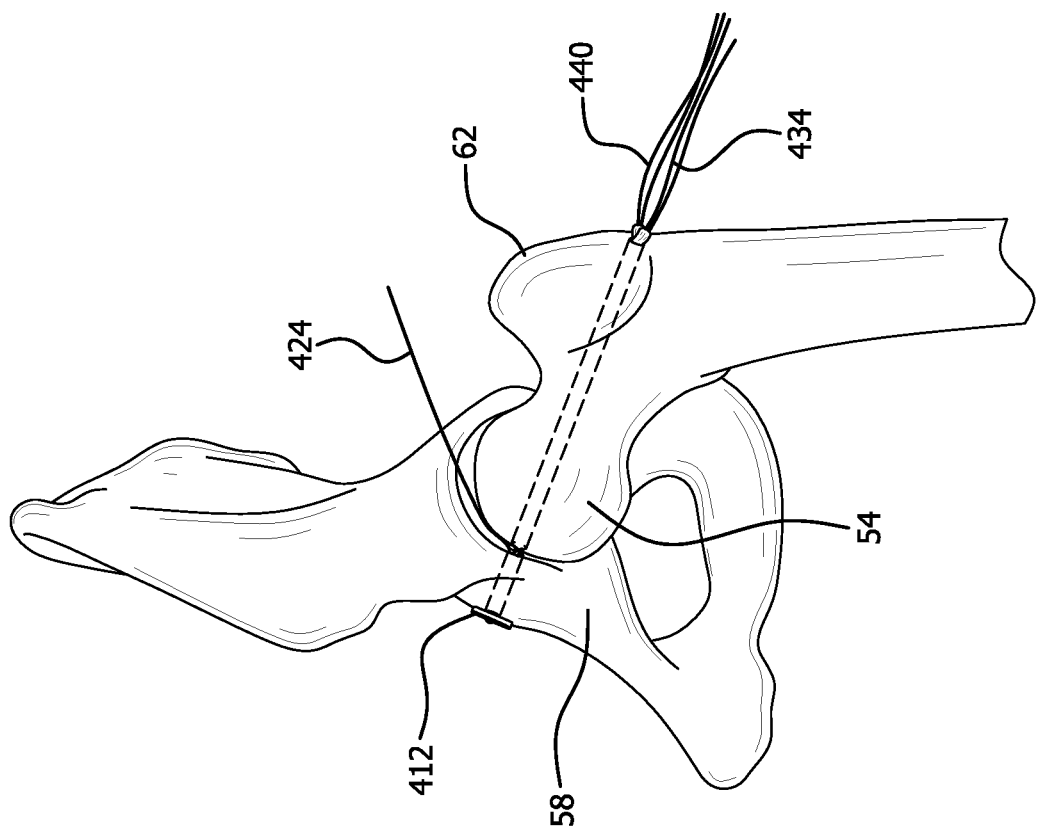
FIG. 20 is a schematic perspective view, partially in phantom, of a second step of a graft insertion procedure through a surgical tunnel in the hip joint as part of a ligamentum teres reconstruction procedure.
Figure 21:
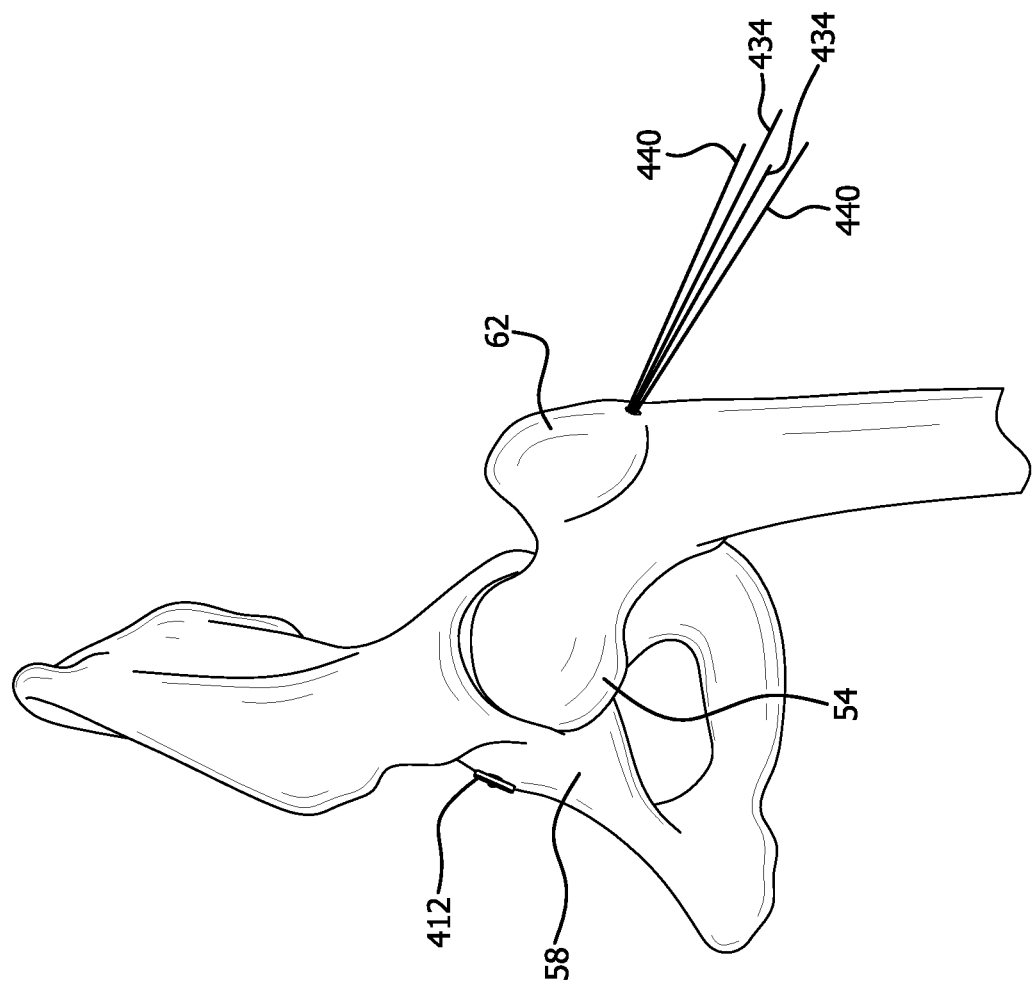
FIG. 21 is a schematic perspective view, partially in phantom, of a third step of a graft insertion procedure through surgical tunnel in the hip joint as part of a ligamentum teres reconstruction procedure.

The ligamentum teres reconstruction procedure can be completed in a suitable fashion. As shown in FIG. 15, a surgical drill bit 364 can be advanced through the acetabulum 58. As shown in FIG. 16, a suitable graft placement device 400 with an elongated shaft 404 and manipulating handle 408 can be used to place surgical button 412 and suture 416 through the opening 362 in the greater trochanter 62, through the surgical tunnel 360 and the acetabulum 58. The surgical button 412 will emerge from opening 368 in acetabulum 58 (FIG. 17). A suture loop 420 will extend proximally from the opening 362 for attachment of the surgical graft or other surgical items for the procedure (FIG. 18). A free end of suture 424 extends laterally for tightening the graft assembly. The surgical graft 430 with sutures 434 and 440 is positioned on the suture loop 420 (FIG. 19). The free end 424 is tensioned to position and tighten the graft in the tunnel 360 (FIG. 20). The sutures 434 and 440 are tightened (FIG. 21), and then secured and trimmed to complete the ligamentum teres reconstruction procedure.

Figure 22:
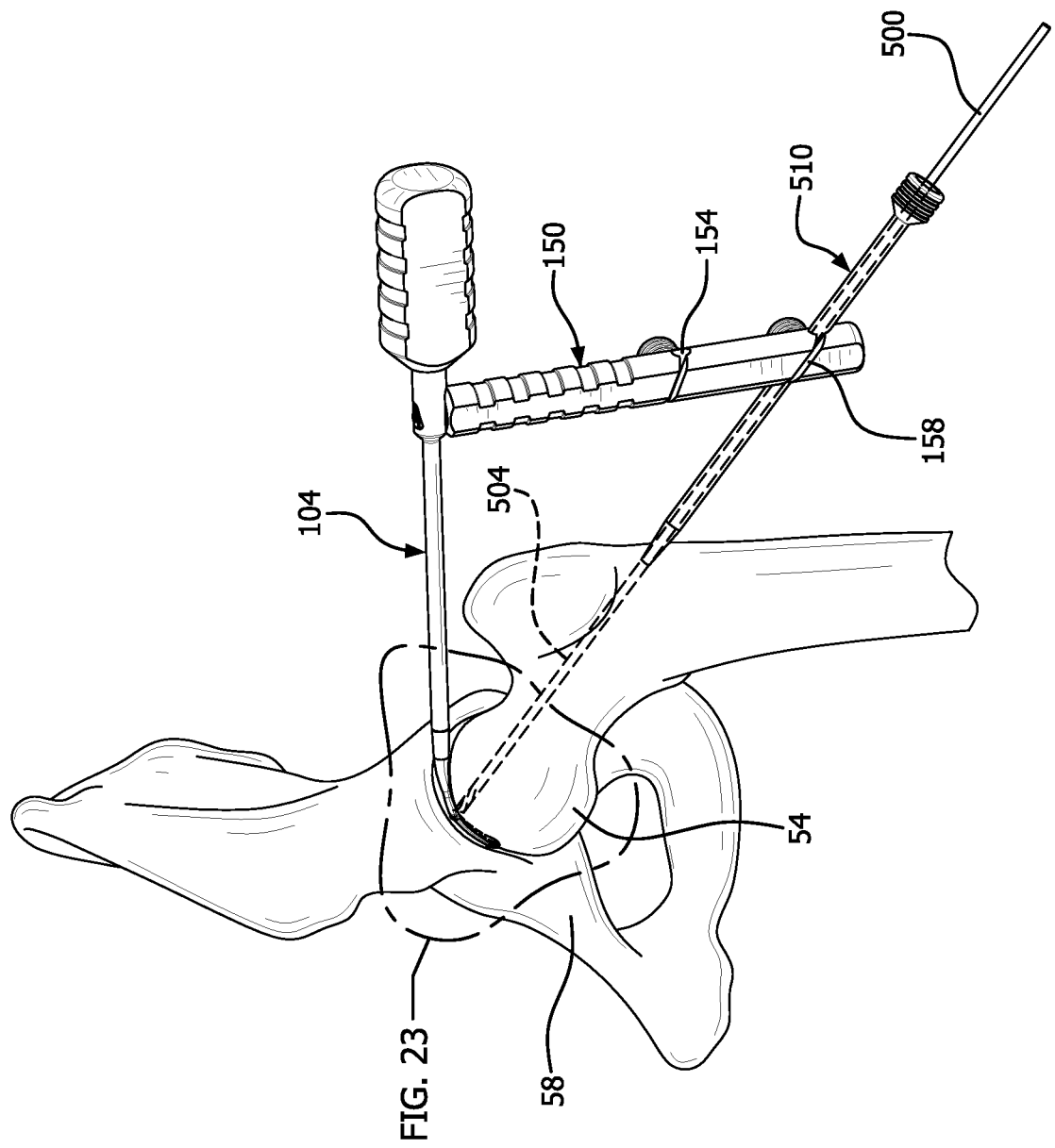
FIG. 22 is a schematic perspective view, partially in phantom, of a drill guide and drill guide insert with a surgical pin in a hip joint as part of an avascular necrosis repair procedure.
Figure 23:
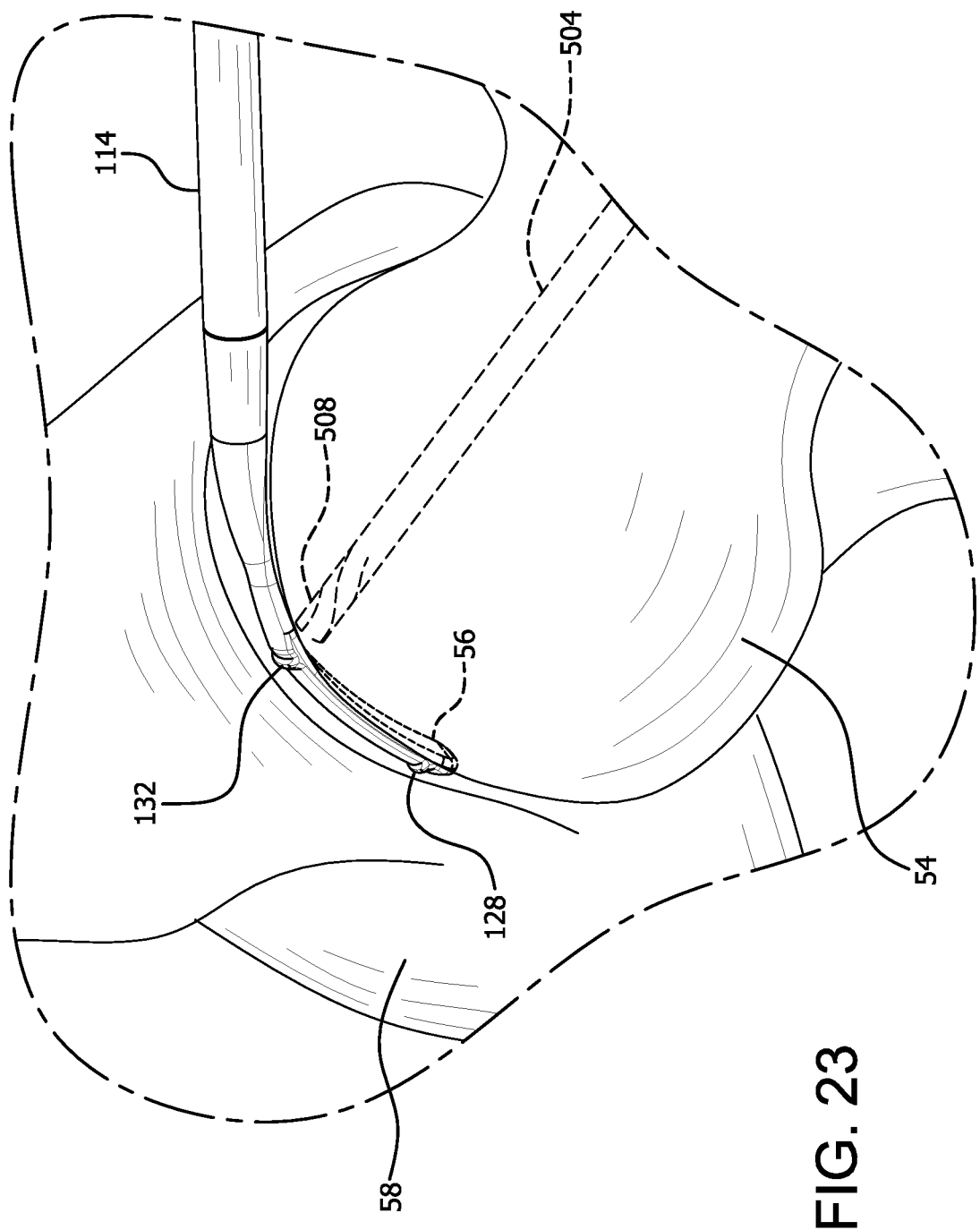
FIG. 23 is an enlarged perspective view, partially in phantom, of area FIG. 23 in FIG. 22.

An avascular necrosis repair procedure is illustrated in FIGS. 22-30. The positioning arm 104 and drill jig 150 can be positioned as previously described. In this instance, the guide opening 158 is used as it aligns with protrusion 132 of locating end 120 to create a surgical tunnel at a location suitable for an avascular necrosis repair procedure. The drill guide opening can have a drill guide insert 200 as was used for the ligamentum teres reconstruction procedure, or can be a dedicated drill guide insert 510 suitable for receiving a surgical pin 500 that is specifically designed for avascular necrosis repair (FIG. 22). The surgical pin 500 is advanced through the femoral head 54 until the tip 508 reaches the locating end 120 and the radiopaque protrusion 132 that is positioned for directing the avascular necrosis repair tunnel (FIG. 23).

Figure 24:
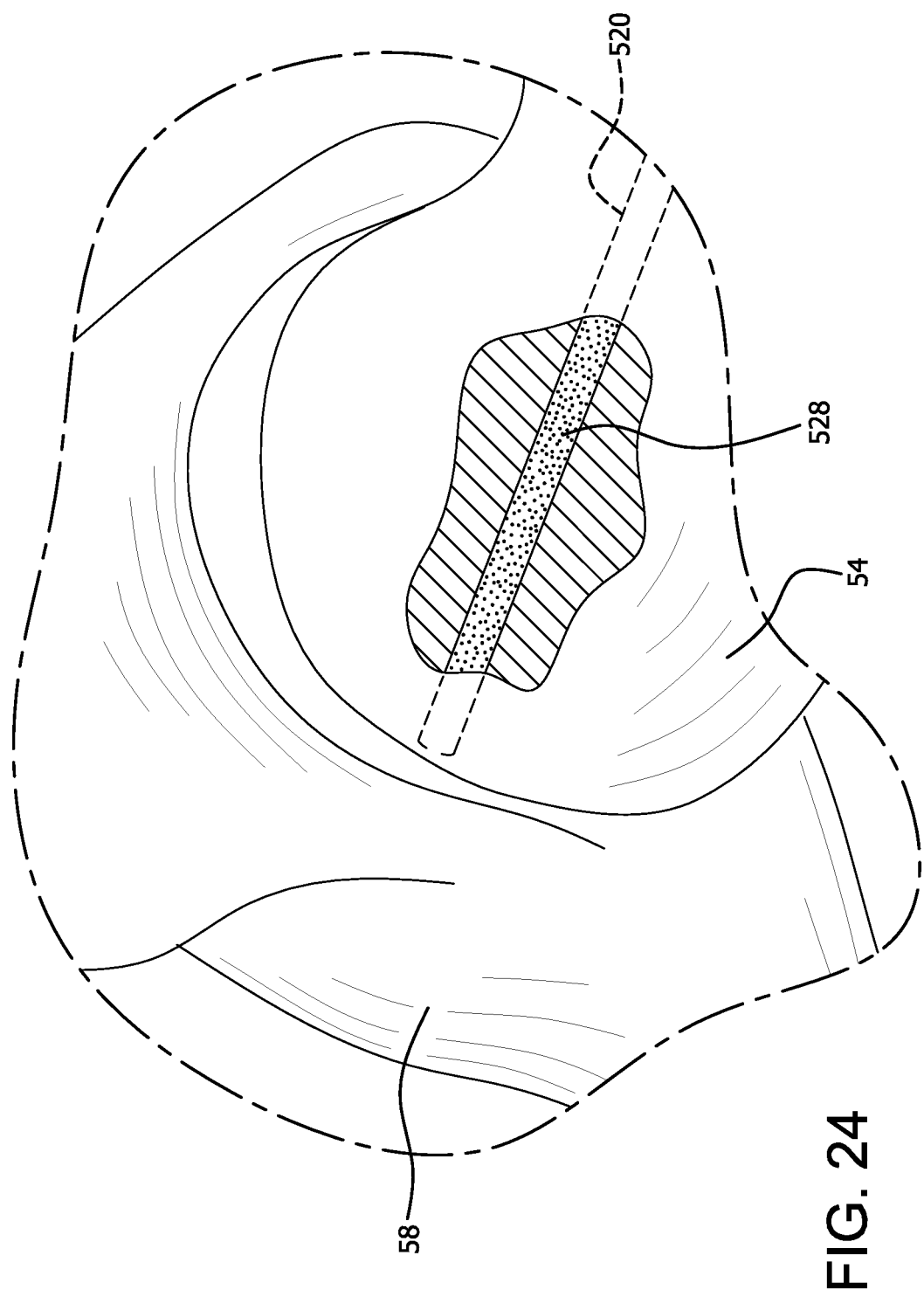
FIG. 24 is an enlarged schematic perspective view, partially in phantom and partially broken away, of a surgical tunnel filled by a bone repair composition as part of an avascular necrosis repair procedure.
Figure 25:
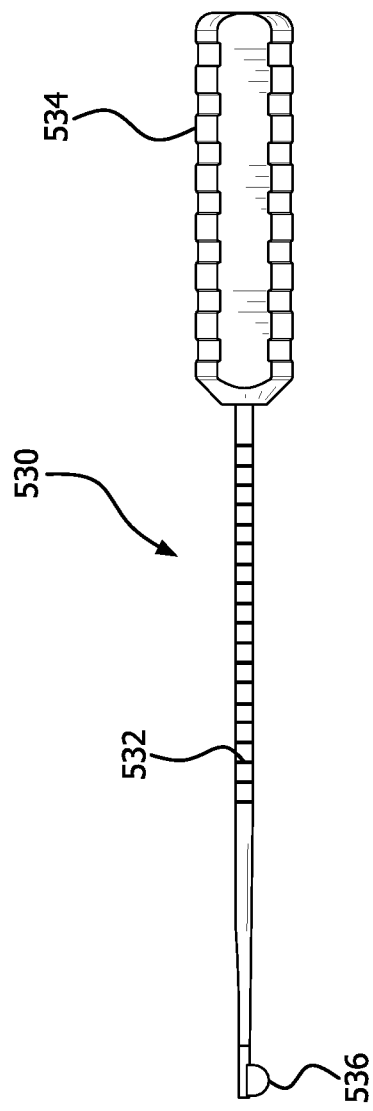
FIG. 25 is a side elevation of a curette.

The surgical pin 500 is appropriately positioned and then a surgical drill bit is advanced (not shown) using the surgical pin 500 as a guide to create an avascular necrosis repair tunnel 520 (FIG. 24). The avascular necrosis repair tunnel 520 is then filled with a bone repair composition 528. Such compositions are known for avascular necrosis repair, and any such composition can be utilized. It is possible to shave spurs and irregularities from the avascular necrosis repair 520 by use of a suitable instrument such as a curette 530 (FIG. 25). The curette 530 can be of any suitable design, such as but not limited to the curette 530 with elongated shaft 532, handle 534 and blade 536.

Figure 26:
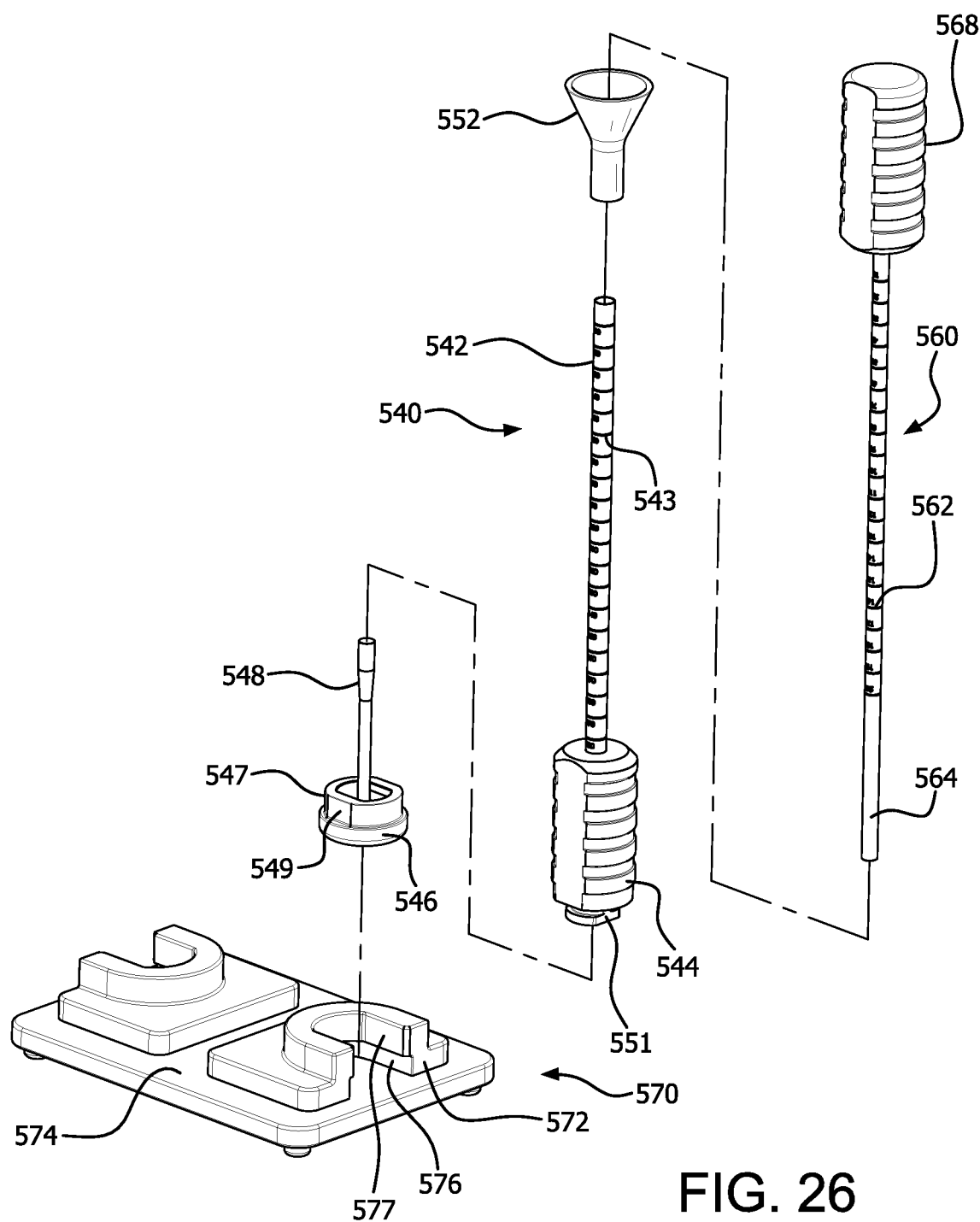
FIG. 26 is an exploded perspective view of a bone repair composition filling assembly.
Figure 27:
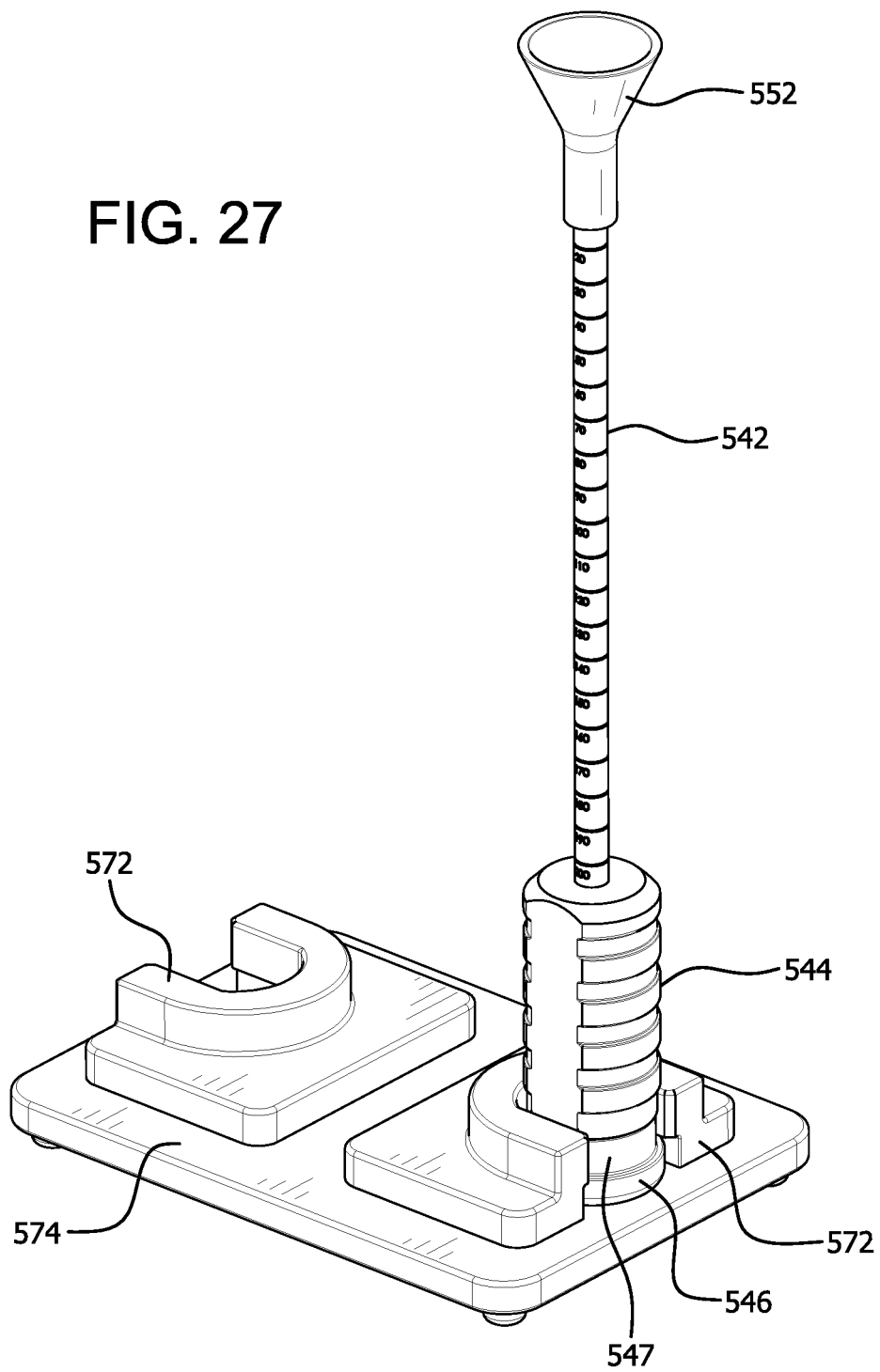
FIG. 27 is a perspective view of a graft hopper, funnel, and support stand.
Figure 28:
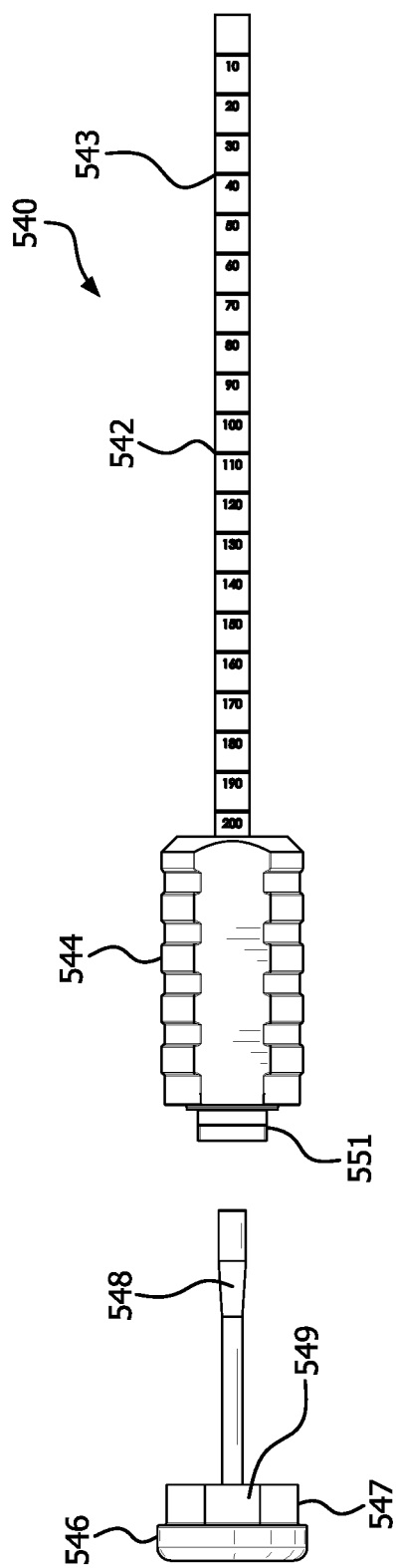
FIG. 28 is an exploded side elevation of a graft hopper.

Suitable apparatus for placing the bone repair composition into the avascular necrosis repair tunnel 520 can be provided. Any suitable apparatus is possible, and an exemplary apparatus is shown in FIGS. 26-30. Suitable apparatus can include a graft hopper 540, a tamper 560 and a support stand 570 (FIG. 26). The graft hopper 540 can include an elongated tubular hopper 542 dimensioned such that it will fit within the avascular necrosis repair tunnel 520. The outside surface of the tubular hopper 542 can include measuring indicia 543 for use in determining the length of insertion of the elongated tubular hopper 542 into the avascular necrosis repair tunnel 520 (FIG. 28). A removable funnel 552 can be provided to assist placement of the bone repair composition into the elongated tubular hopper 542. A handle 544 can be provided and has a fitting 551 comprising an open bore for communicating with the open interior of the elongated tubular hopper 542. The open bore allows access to the length of the elongated tubular hopper 542 for removing the bone repair composition from the elongated tubular hopper 542, as will be described. This proximal opening can also be used for cleaning, sterilization and other purposes.

A cap 546 can be provided with a plug 548 for closing the open bore of the fitting 551 and can engage the fitting 551 by any suitable means such as threads or a press fit provided by an engagement structure 547. A flattened surface 549 can be provided to engage fitting 572 provided on base 574 of support stand 570. The cap 546 will engage slots 576 of fittings 572 and the flattened surface 549 will mate with flattened surface 577 of the fitting 572. In this manner the graft hopper 540 will be held in the upright position to facilitate filling with the bone repair composition (FIG. 27).

Figure 29:
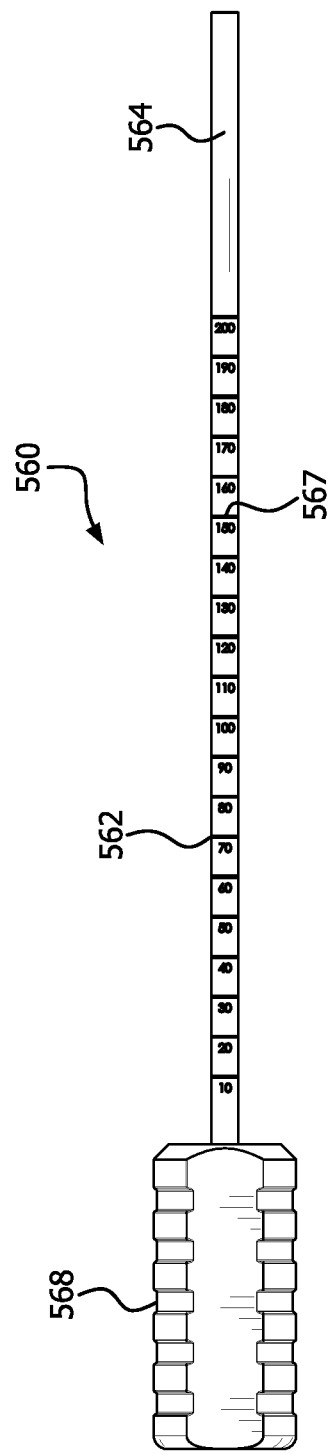
FIG. 29 is a side elevation of a tamper.
Figure 30:
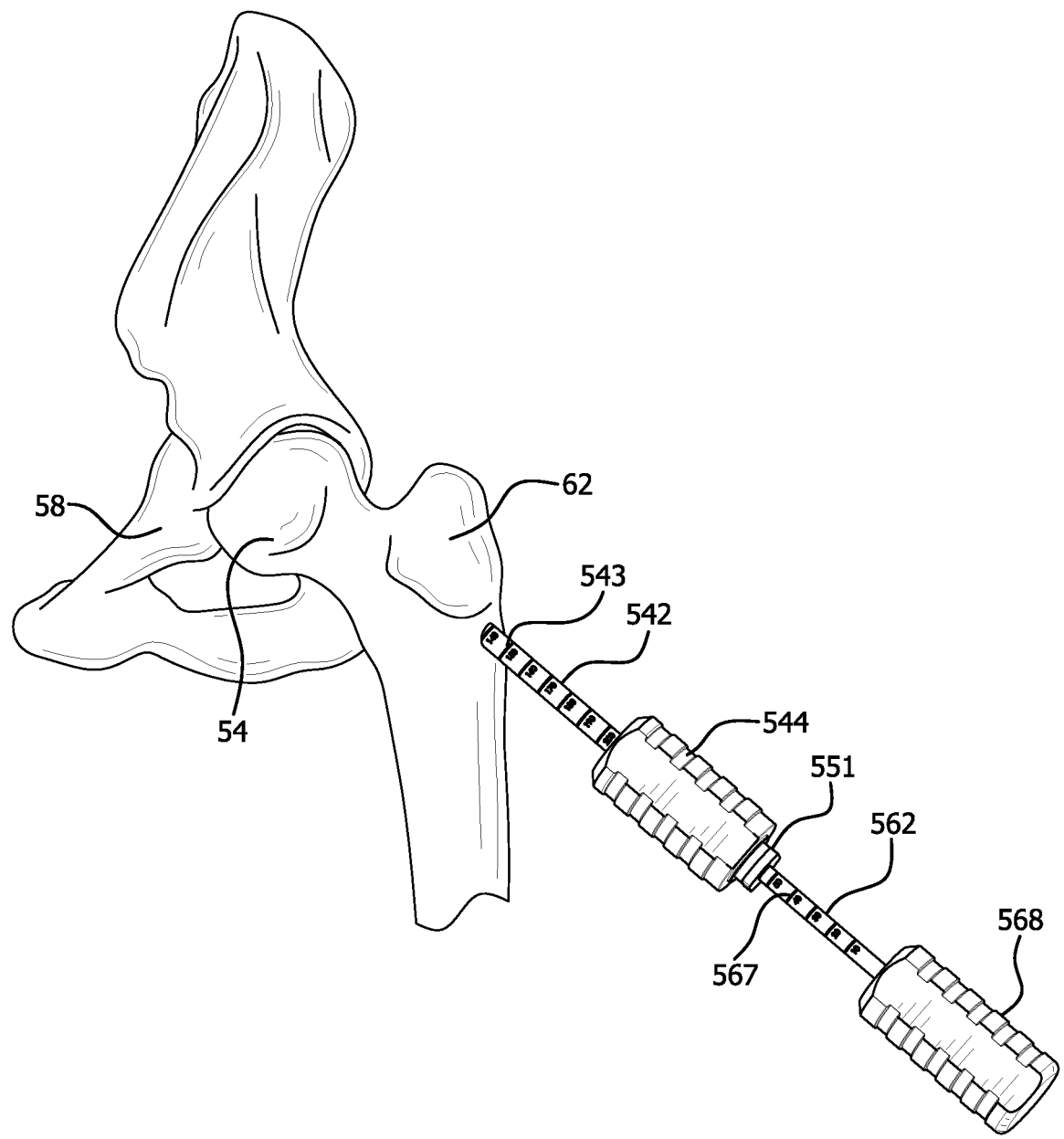
FIG. 30 is a schematic perspective view of the filling assembly in use in a hip joint as part of an avascular necrosis repair procedure.

The tamper 560 includes an elongated tamper shaft 562 with tip 564 and a handle 568 (FIG. 29). The shaft 562 can include indicia 567 for determining the insertion depth of the tamper shaft 562. The tamper 560 can be used to place the bone repair composition in the elongated tubular hopper 542. The tamper 560 is more particularly used to push the bone repair composition from the elongated tubular hopper 542 during the avascular necrosis repair procedure. As shown in FIG. 30, the elongated tubular hopper 542 is inserted into the avascular necrosis repair tunnel 520 at the greater trochanter 62. The cap 546 is removed from the fitting 551 and the tamper shaft 562 is inserted through the bore in the fitting 551 into the elongated tubular hopper 542. The tamper shaft 562 can be advanced to push the bone repair composition out of the elongated tubular hopper 542 into the avascular necrosis repair tunnel 520. The indicia 543 on the outside surface of the elongated tubular hopper 542 and the indicia 567 on the tamper shaft 562 are used to gauge both the position of the bone repair composition in the avascular necrosis repair tunnel 520 and the amount of the bone repair composition that has been pushed from the elongated tubular hopper 542. Other structures are possible.

Figure 31:
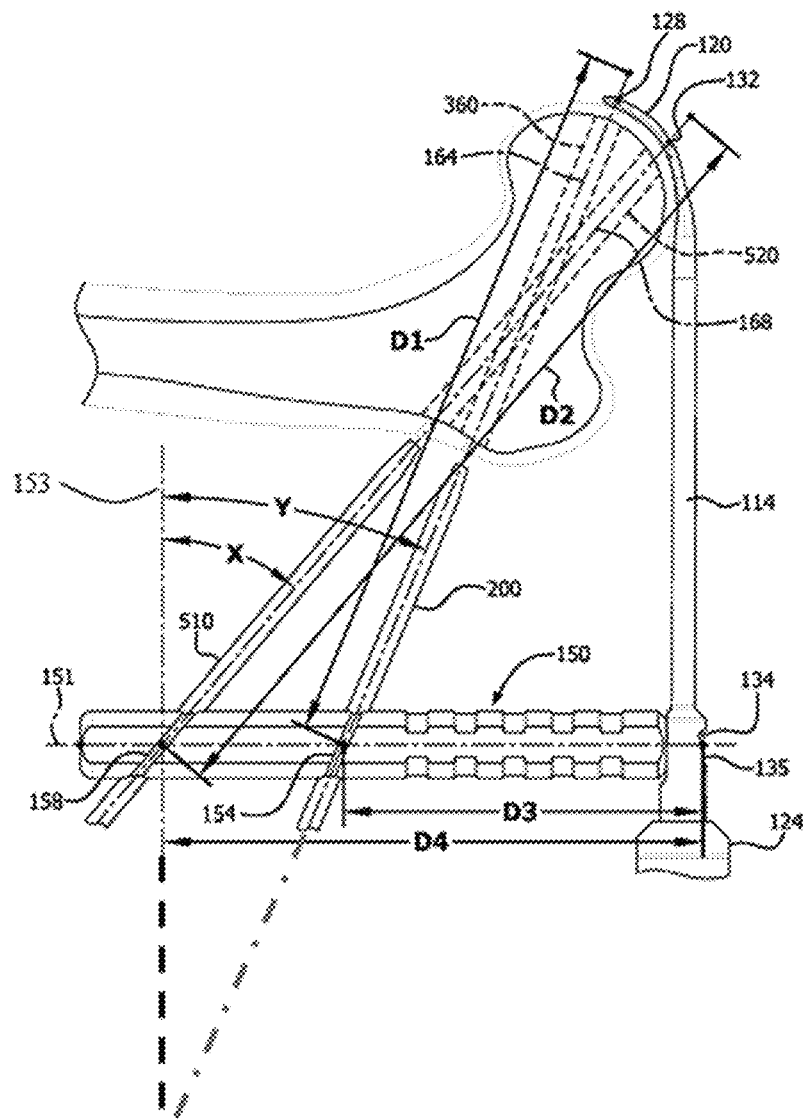
FIG. 31 is a schematic side elevation, partially in phantom, of a drill guide and femoral head illustrating drill element guide axes and drill guide opening locations.

The drill jig can include drill guide openings for both the ligamentum teres reconstruction procedure, and for the avascular necrosis repair procedure. This is shown in FIG. 31. The drill jig can have a first drill guide opening 154 with a drill element guide axis from 15 to 30 degrees from a normal 153 to the drill jig axis 151, indicated by "Y" in FIG. 31, and a second drill guide opening 158 with a drill element guide axis from 35 to 45 degrees from a normal 153 to the drill jig axis 151, indicated by "X" in FIG. 31. The first drill guide opening can be positioned on the drill jig laterally outward from the second drill guide opening with respect to the engagement end of the drill jig. The first drill guide opening 154 can be positioned a distance D1 of from 7 to 9 inches from the marker protrusion 128 at the locating end 120, and a distance D3 of from 3 to 5 inches from the side 135 of the engagement body 133 of the positioning arm and the engagement end of the drill jig 150, for a ligamentum teres reconstruction procedure. The second drill guide opening 158 can be positioned a distance D2 of from 8 to 10 inches from marker protrusion 132 at the locating end 120, and a distance D4 of from 5 to 7 inches from the side of the positioning arm and the engagement end of the drill jig for an avascular necrosis repair procedure. The drill jig and the positioning arm can define a plane, and the drill element guide axis lies can lie in that plane. The drill element guide axis of one drill guide opening can intersect the drill element guide axis of another drill guide opening because the guide openings are not used simultaneously.

The invention as shown in the drawings and described in detail herein disclose arrangements of elements of particular construction and configuration for illustrating preferred embodiments of structure and method of operation of the present invention. It is to be understood however, that elements of different construction and configuration and other arrangements thereof, and methods of operation other than those illustrated and described may be employed in accordance with the spirit of the invention, and such changes, alterations and modifications as would occur to those skilled in the art are considered to be within the scope of this invention as broadly defined in the appended claims. In addition, it is to be understood that the phraseology and terminology employed herein are for the purpose of description and should not be regarded as limiting.

We claim:
1. A minimally invasive surgical drill guide, comprising:
an elongated drill jig comprising at an engagement end thereof engagement structure, the drill jig comprising a drill guide opening for defining a location and drill element guide axis for placement of a surgical drill element; and,
a positioning arm having an elongated shaft with an axis and a locating end portion at a distal end for engaging a bony part of a patient, and an elongated grasping handle at a proximal end of the elongated shaft and axially aligned with the elongated shaft for manipulating the position of the elongated shaft and the locating end, the elongated shaft comprising engagement structure between the handle and the locating end, the engagement structure of the drill jig detachably engaging the engagement structure of the positioning arm crosswise to support the drill guide opening of the drill jig at a location remote from the axis of the elongated shaft;
wherein the elongated drill jig comprises a plurality of drill guide openings and the locating end comprises a radiopaque marker associated with each drill guide opening, the drill element guide axis of each drill guide opening intercepting the associated radiopaque marker, and wherein the drill element guide axis of one drill guide opening intersects the drill element guide axis of another drill guide opening.

2. The surgical drill guide of claim 1, further comprising an elongated drill guide insert having an elongated open interior drill guide passage for receiving the surgical drill element, the drill guide insert being dimensioned for placement in the drill guide opening of the drill jig, the drill jig and the drill guide insert comprising cooperating securing structure for securing the drill guide insert within the drill guide opening.

3. The surgical drill guide of claim 2, wherein the interior drill guide passage is dimensioned for a surgical drill guide pin.

4. The surgical drill guide of claim 1, wherein the drill guide openings comprises a channel having the drill element guide axis aligned with the locating end, whereby when a surgical drill element is advanced through the drill guide opening the drill element will advance along the drill element guide axis toward the locating end.

5. The surgical drill guide of claim 1, wherein the locating end is shaped to mate with a bony part of the patient.

6. The surgical drill guide of claim 1, wherein the locating end is curved.

7. The surgical drill guide of claim 6, wherein the curved locating end is configured to mate with a portion of the femoral head.

8. The surgical drill guide of claim 7, wherein the curved locating end is configured to mate with the fovea.

9. The surgical drill guide of claim 1, wherein the elongated drill jig comprises a long axis, and the drill element guide axis is from 35 to 45 degrees from a normal to the drill jig axis.

10. The surgical drill guide of claim 1, wherein the elongated drill jig comprises a long axis, and the drill element guide axis is from 15 to 30 degrees from a normal to the drill jig axis.

11. The surgical drill guide of claim 1, wherein the radiopaque marker comprises a radiopaque protrusion.

12. The surgical drill guide of claim 11, wherein the raised protrusion comprises at least one radiopaque ridge.

13. The surgical drill guide of claim 1, wherein the elongated drill jig comprises a long axis, and the drill element guide axis of a first drill guide opening is from 35 to 45 degrees from a normal to the drill jig axis, and the drill element guide axis of a second drill guide opening is from 15 to 30 degrees from a normal to the drill jig axis.

14. The surgical drill guide of claim 13, wherein the first drill guide opening is positioned on the drill jig laterally outward from the second drill guide opening with respect to the engagement end of the drill jig.

15. The surgical drill guide of claim 13, wherein the first drill guide opening is positioned 5 to 7 inches from the engagement end of the drill jig, and the second drill guide opening is positioned 3 to 5 inches from the engagement end of the drill jig.

16. The surgical drill guide of claim 1, wherein the drill jig and the positioning arm define a plane, and the drill element guide axis lies in the plane.

17. A ligamentum teres reconstruction system, comprising:
an elongated drill jig comprising at an engagement end thereof engagement structure, the drill jig comprising a drill guide opening for defining a location and drill element guide axis for placement of a surgical drill element; and;
a positioning arm having an elongated shaft with an axis and a locating end portion at a distal end configured to engage a part of the femoral head of a patient, and an elongated grasping handle at a proximal end for manipulating the position of the elongated shaft and the locating end, the shaft comprising engagement structure between the handle and the locating end, the engagement structure of the drill jig detachably engaging the engagement structure of the positioning arm crosswise to support the drill guide opening of the drill jig at a location remote from the axis of the elongated shaft;
wherein the elongated drill jig comprises a long axis, and the drill element guide axis is from 15 to 30 degrees from a normal to the drill jig axis, and wherein the drill guide opening is positioned 3 to 5 inches from the engagement end of the drill jig.

18. The ligamentum teres reconstruction system of claim 17, wherein the drill jig is detachable from the positioning arm.

19. The ligamentum teres reconstruction system of claim 17, wherein the locating end comprises a radiopaque marker.

20. The ligamentum teres reconstruction system of claim 19, wherein the radiopaque marker comprises a radiopaque protrusion.

21. The ligamentum teres reconstruction system of claim 17, further comprising an elongated drill guide insert having an elongated open interior drill guide passage for receiving the surgical drill element, the drill guide insert being dimensioned for placement in the drill guide opening of the drill jig, the drill jig and the drill guide insert comprising cooperating securing structure for securing the drill guide insert within the drill guide opening.

22. The ligamentum teres reconstruction system of claim 17, wherein the locating end is curved.

23. The ligamentum teres reconstruction system of claim 22, wherein the curved locating end is configured to mate with a portion of the femoral head.

24. The ligamentum teres reconstruction system of claim 23, wherein the curved locating end is configured to mate with the fovea.

25. An avascular necrosis repair system, comprising:
an elongated drill jig comprising at an engagement end thereof engagement structure, the drill jig comprising a drill guide opening for defining a location and drill element guide axis for placement of a surgical drill element; and;
a positioning arm having an elongated shaft with an axis and a locating end portion at a distal end configured to engage a part of the femoral head of a patient, and an elongated grasping handle at a proximal end for manipulating the position of the elongated shaft and the locating end, the shaft comprising engagement structure between the handle and the locating end, the engagement structure of the drill jig detachably engaging the engagement structure of the positioning arm crosswise to support the drill guide opening of the drill jig at a location remote from the axis of the elongated shaft;
wherein the elongated drill jig comprises a long axis, and the drill element guide axis is from 35 to 45 degrees from a normal to the drill jig axis, and wherein the drill guide opening is positioned 5 to 7 inches from the engagement end of the drill jig.

26. The avascular necrosis repair system of claim 25, wherein the drill jig is detachable from the positioning arm.

27. The avascular necrosis repair system of claim 25, wherein the locating end comprises a radiopaque marker.

28. The avascular necrosis repair system of claim 27, wherein the radiopaque marker comprises a radiopaque protrusion.

29. The avascular necrosis repair system of claim 25, further comprising an elongated drill guide insert having an elongated open interior drill guide passage for receiving the surgical drill element, the drill guide insert being dimensioned for placement in the drill guide opening of the drill jig, the drill jig and the drill guide insert comprising cooperating securing structure for securing the drill guide within the drill guide opening.

30. The avascular necrosis repair system of claim 25, wherein the locating end is curved.

31. The avascular necrosis repair system of claim 30, wherein the curved locating end is configured to mate with a portion of the femoral head.

32. A minimally invasive surgical drill guide, comprising:
an elongated drill jig comprising at an engagement end thereof engagement structure, the drill jig comprising a drill guide opening for defining a location and drill element guide axis for placement of a surgical drill element; and,
a positioning arm having an elongated shaft with an axis and a locating end portion at a distal end for engaging a bony part of a patient, and an elongated grasping handle at a proximal end of the elongated shaft and axially aligned with the elongated shaft for manipulating the position of the elongated shaft and the locating end, the elongated shaft comprising engagement structure between the handle and the locating end, the engagement structure of the drill jig detachably engaging the engagement structure of the positioning arm crosswise to support the drill guide opening of the drill jig at a location remote from the axis of the elongated shaft;
wherein the handle is detachable from the elongated shaft, and wherein the handle comprises engagement structure, the elongated shaft comprises a transverse opening and an intersecting axial opening, and wherein engagement structure of the handle is configured to be received within the axial opening of the elongated shaft, the engagement structure of the drill jig is configured to be received within the transverse opening of the elongated shaft, and wherein the engagement structure of the handle engages the engagement structure of the drill jig to secure the drill jig and the handle to the elongated shaft.

33. A ligamentum teres reconstruction system, comprising:
an elongated drill jig comprising at an engagement end thereof engagement structure, the drill jig comprising a drill guide opening for defining a location and drill element guide axis for placement of a surgical drill element;
and
a positioning arm having an elongated shaft with an axis and a locating end portion at a distal end configured to engage a part of the femoral head of a patient, and an elongated grasping handle at a proximal end for manipulating the position of the elongated shaft and the locating end, the shaft comprising engagement structure between the handle and the locating end, the engagement structure of the drill jig detachably engaging the engagement structure of the positioning arm crosswise to support the drill guide opening of the drill jig at a location remote from the axis of the elongated shaft, wherein the handle is detachable from the elongated shaft.

34. The ligamentum teres reconstruction system of claim 33, wherein the handle comprises engagement structure, the elongated shaft comprises a transverse opening and an intersecting axial opening, and wherein engagement structure of the handle is configured to be received within the axial opening of the elongated shaft, the engagement structure of the drill jig is configured to be received within the transverse opening of the elongated shaft, and wherein the engagement structure of the handle engages the engagement structure of the drill jig to secure the drill jig and the handle to the elongated shaft.

35. An avascular necrosis repair system, comprising:
an elongated drill jig comprising at an engagement end thereof engagement structure, the drill jig comprising a drill guide opening for defining a location and drill element guide axis for placement of a surgical drill element; and,
a positioning arm having an elongated shaft with an axis and a locating end portion at a distal end configured to engage a part of the femoral head of a patient, and an elongated grasping handle at a proximal end for manipulating the position of the elongated shaft and the locating end, the shaft comprising engagement structure between the handle and the locating end, the engagement structure of the drill jig detachably engaging the engagement structure of the positioning arm crosswise to support the drill guide opening of the drill jig at a location remote from the axis of the elongated shaft,
wherein the handle is detachable from the elongated shaft, and wherein the handle comprises engagement structure, the elongated shaft comprises a transverse opening and an intersecting axial opening, and wherein engagement structure of the handle is configured to be received within the axial opening of the elongated shaft, the engagement structure of the drill jig is configured to be received within the transverse opening of the elongated shaft, and wherein the engagement structure of the handle engages the engagement structure of the drill jig to secure the drill jig and the handle to the elongated shaft.

\* \* \* \* \*